(12) United States Patent
Ramsay et al.

(10) Patent No.: US 11,734,911 B2
(45) Date of Patent: *Aug. 22, 2023

(54) SYSTEM AND METHOD FOR THE VISUALIZATION AND CHARACTERIZATION OF OBJECTS IN IMAGES

(71) Applicant: Imago Systems, Inc., Summit, NJ (US)

(72) Inventors: Thomas E. Ramsay, Leesburg, VA (US); Eugene B. Ramsay, Tucson, AZ (US)

(73) Assignee: Imago Systems, Inc., Lansdowne, VA (US)

( * ) Notice: Subject to any disclaimer, the term of this patent is extended or adjusted under 35 U.S.C. 154(b) by 125 days.

This patent is subject to a terminal disclaimer.

(21) Appl. No.: 17/129,133

(22) Filed: Dec. 21, 2020

(65) Prior Publication Data

US 2021/0258451 A1 Aug. 19, 2021

Related U.S. Application Data

(63) Continuation of application No. 15/533,451, filed as application No. PCT/US2017/016999 on Feb. 8, 2017, now Pat. No. 10,873,681.

(Continued)

(51) Int. Cl.
*G06K 9/46* (2006.01)
*G06V 10/54* (2022.01)
(Continued)

(52) U.S. Cl.
CPC ............ *G06V 10/54* (2022.01); *A61B 5/4312* (2013.01); *A61B 6/502* (2013.01); *A61B 6/5217* (2013.01);
(Continued)

(58) Field of Classification Search
CPC ... A61B 2503/40; A61B 5/4312; A61B 6/502; A61B 6/5217; A61B 8/0825;
(Continued)

(56) References Cited

U.S. PATENT DOCUMENTS 5,854,851 A 12/1998 Bamberger et al.
6,031,935 A 2/2000 Kimmel
(Continued)

FOREIGN PATENT DOCUMENTS

JP 2003158677 5/2003
JP 2005111946 4/2005
(Continued)

OTHER PUBLICATIONS

International Patent Application No. PCT/US2017/016999; Notification of the International Search Report and the Written Opinion of the International Searching Authority, or the Declaration, dated Apr. 13, 20017, 7 pages.
(Continued)

*Primary Examiner* — Christopher L Cook
(74) *Attorney, Agent, or Firm* — Morgan, Lewis & Bockius LLP

(57) ABSTRACT

A method of visualization, characterization, and detection of objects within an image by applying a local micro-contrast convergence algorithm to a first image to produce a second image that is different from the first image, wherein all like objects converge into similar patterns or colors in the second image.

7 Claims, 29 Drawing Sheets

Resultant image after CI PLUT 2

Related U.S. Application Data

(60) Provisional application No. 62/292,413, filed on Feb. 8, 2016.

(51) Int. Cl.

| | | |
|---|---|---|
| *A61B 8/08* | (2006.01) | |
| *A61B 6/00* | (2006.01) | |
| *G06T 7/00* | (2017.01) | |
| *G06T 7/48* | (2017.01) | |
| *G06V 10/56* | (2022.01) | |
| *G06V 10/46* | (2022.01) | |
| *G06T 7/11* | (2017.01) | |
| *G06T 7/174* | (2017.01) | |
| *A61B 5/00* | (2006.01) | |
| *G06T 11/00* | (2006.01) | |
| *H04N 1/46* | (2006.01) | |
| *H04N 1/60* | (2006.01) | |

(52) U.S. Cl.
CPC .......... *A61B 8/0825* (2013.01); *A61B 8/5223* (2013.01); *G06T 7/0012* (2013.01); *G06T 7/11* (2017.01); *G06T 7/174* (2017.01); *G06T 7/48* (2017.01); *G06T 11/001* (2013.01); *G06V 10/462* (2022.01); *G06V 10/56* (2022.01); *H04N 1/465* (2013.01); *H04N 1/6027* (2013.01); *A61B 2503/40* (2013.01); *G06T 2207/10116* (2013.01); *G06T 2207/30016* (2013.01); *G06T 2207/30056* (2013.01); *G06T 2207/30061* (2013.01); *G06T 2207/30068* (2013.01); *G06T 2207/30081* (2013.01); *G06T 2207/30084* (2013.01); *G06T 2207/30096* (2013.01); *G06V 2201/03* (2022.01)

(58) Field of Classification Search
CPC ................ A61B 8/5223; G06T 11/001; G06T 2207/10116; G06T 2207/30016; G06T 2207/30056; G06T 2207/30061; G06T 2207/30068; G06T 2207/30081; G06T 2207/30084; G06T 2207/30096; G06T 7/0012; G06T 7/11; G06T 7/174; G06T 7/48; G06V 10/462; G06V 10/54; G06V 10/56; G06V 2201/03; G16H 50/30; H04N 1/465; H04N 1/6027

See application file for complete search history.

(56) References Cited

U.S. PATENT DOCUMENTS

| | | |
|---|---|---|
| 6,249,594 B1 | 6/2001 | Hibbard |
| 7,492,937 B2 | 2/2009 | Ramsay et al. |
| 7,496,218 B2 | 2/2009 | Ramsay et al. |
| 7,805,183 B2 | 9/2010 | Keely et al. |
| 7,817,833 B2 | 10/2010 | Ramsay et al. |
| 7,840,048 B2 | 11/2010 | Ramsay et al. |
| 7,907,762 B2 | 3/2011 | Ramsay et al. |
| 7,916,912 B2 | 3/2011 | Abramov et al. |
| 7,949,181 B2 | 5/2011 | Padfield et al. |
| 8,045,176 B2 | 10/2011 | Everett et al. |
| 8,045,805 B2 | 10/2011 | Ramsay et al. |
| 8,295,575 B2 | 10/2012 | Feldman et al. |
| 8,340,471 B2 | 12/2012 | Furukawa et al. |
| 8,341,100 B2 | 12/2012 | Miller et al. |
| 8,358,453 B2 | 1/2013 | Mestha et al. |
| 8,538,099 B2 | 9/2013 | Fessler et al. |
| 8,571,287 B2 | 10/2013 | DeMan et al. |
| 8,582,916 B2 | 11/2013 | Bar-Aviv et al. |
| 8,594,444 B2 | 11/2013 | Geiger et al. |
| 8,660,330 B2 | 2/2014 | Jarisch |
| 8,705,833 B2 | 4/2014 | Yagi et al. |
| 8,718,340 B2 | 5/2014 | Madabhushi et al. |
| 8,897,528 B2 | 11/2014 | Benson et al. |
| 8,897,544 B2 | 11/2014 | Christopher et al. |
| 9,111,179 B2 | 8/2015 | Janowczyk et al. |
| 9,159,129 B2 | 10/2015 | Schoenmeyer et al. |
| 9,256,977 B2 | 2/2016 | Rehwald et al. |
| 9,310,302 B2 | 4/2016 | Garsha et al. |
| 9,401,019 B2 | 7/2016 | Dennerlein et al. |
| 2002/0025066 A1 | 2/2002 | Pettigrew |
| 2005/0078861 A1 | 4/2005 | Usikov et al. |
| 2005/0123181 A1 | 6/2005 | Freund et al. |
| 2006/0078926 A1 | 4/2006 | Marcelpoil et al. |
| 2006/0127880 A1 | 6/2006 | Harris et al. |
| 2008/0015448 A1 | 1/2008 | Keely et al. |
| 2008/0085040 A1 | 4/2008 | Basu et al. |
| 2009/0092298 A1 | 4/2009 | Xu et al. |
| 2009/0324067 A1 | 12/2009 | Ramsay et al. |
| 2010/0266179 A1* | 10/2010 | Ramsay ................ G06T 7/0012 382/131 |
| 2011/0026789 A1 | 2/2011 | Hsu et al. |
| 2011/0052032 A1 | 3/2011 | Ramsay et al. |
| 2011/0060755 A1 | 3/2011 | Mollus et al. |
| 2011/0274327 A1 | 11/2011 | Wehnes et al. |
| 2012/0105430 A1 | 5/2012 | Waschbuesch et al. |
| 2013/0202168 A1 | 8/2013 | Jerebko et al. |
| 2014/0086382 A1 | 3/2014 | Flohr et al. |
| 2014/0205163 A1 | 7/2014 | Stark et al. |
| 2014/0233826 A1 | 8/2014 | Agaian |
| 2014/0314301 A1 | 10/2014 | Azar et al. |
| 2015/0023580 A1 | 1/2015 | Wehnes et al. |
| 2016/0098589 A1 | 4/2016 | Brieu |
| 2016/0253466 A1 | 9/2016 | Agaian et al. |

FOREIGN PATENT DOCUMENTS

| | | |
|---|---|---|
| JP | 2008067296 | 3/2008 |
| WO | 2008157843 A1 | 12/2008 |

OTHER PUBLICATIONS

Ganesan et al. "Computer-aided breast cancer detection using mammograms a review." In: IEEE Reviews in Biomedical Engineering, Dec. 11, 2012, 22 pages.

Liao et al., "A Segmentation Method for Lung Parenchyma Image Sequences Based on Superpixels and a Self-Generating Neural Forest," PloS One, 11.8, Aug. 17, 2016, 25 pages.

Ha et al., "An algorithm to compute independent sets of voxels for parallelization of ICD-based statistical iterative reconstruction," The 13th International Meeting on Fully Three-Dimensional Image Reconstruction in Radiology and Nuclear Medicine, 2015, 4 pages.

Marchesini et al. "X-ray image reconstruction from a diffraction pattern alone," Physical Review B, 68, Oct. 2003, 4 pages.

Extended European Search Report dated Jul. 5, 2019 for European Patent Application No. 17750690.4, 8 pages.

International Preliminary Report on Patentability dated Aug. 14, 2018 for International Application No. PCT/US2017/016999, 5 pages.

Baecker "Image processing and analysis with ImageJ and MRI Cell Image Analyzer." In: Montpellier RIO Imaging, Oct. 20, 2008., [online] [retrieved on Oct. 4, 2018 45), 52 (Oct. 4, 2018)] Retrieved from the Internet y <URL:https://www.unige.ch/medecine/bioimaging/files/5714/1208/5898/Basics.pdf>, entire document, especially Abstract; p. 9-16, 27, 30-40, 50-55, 66.

International Search Report dated Oct. 5, 2018 for International Patent Application No. PCT/US2018/045567, 3 pages.

Written Opinion dated Oct. 5, 2018 for International Patent Application No. PCT/US2018/045567, 10 pages.

First Examination Report dated May 29, 2020 for European Patent Application No. 17750690.4, 8 pages.

Strickland: "Image-processing techniques for tumor detection", Image-Processing Techniques for Tumor Detection, Apr. 24, 2002 (Apr. 24, 2002), pp. 154-155, XP55697624, DOI: https://doi.org/10.1201/9780203909355 ISBN: 978-0-8247-0637-1 Retrieved from the Internet: URL:https://www.taylorfrancis.com/books/9780203909355 [retrieved an May 21, 2020].

(56) References Cited

OTHER PUBLICATIONS

"Applied Research Indicates that BCDx Breast Cancer Detector Technology Routinely Diagnoses Ductal Carcinoma in Situ", available online Apr. 20, 2015 (Year: 2015).
Glasbey-ImageJ, accessed online at https://imagej.net/Glasbey on Nov. 7, 2018.
Glasbey et al., "Colour displays for categorical images", Oct. 26, 2006.
Color Processing: From ImageJ, available online, for example, Dec. 9, 2015, accessed online at https://imagej.net/Color_Image_Processing.
Freedman et al., "Digital Mammography: Tradeoffs between 50 and 100 micron pixel size", May 1995.
First Office Action dated May 28, 2021 for Chinese Patent Application No. 201780022416.5, 10 pages.
Notice of Reason for Rejection dated Aug. 2, 2021 for Japanese Patent Application No. 2018-560735, 10 pages.

\* cited by examiner

Mammogram with pathology-validated cancer

Local micro-contrast processed images showing visualizations of the malignant lesion, defining its irregular boundaries

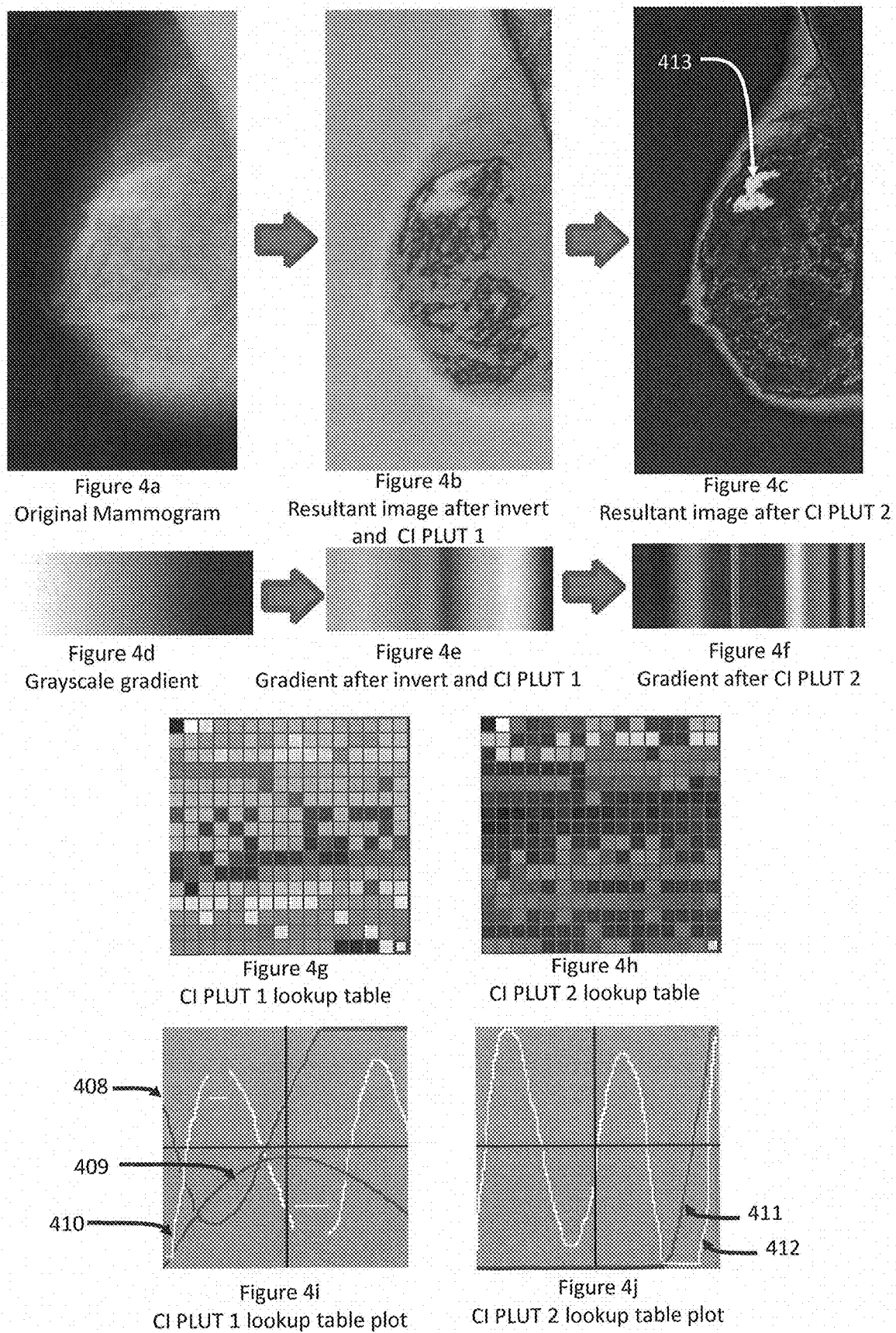

Original Mammogram

Resultant image after LD PLUT 1

Resultant image
after LD HLS adjustment

Grayscale gradient

Gradient after LD PLUT 1

Gradient after LD HLS adjustment

LD PLUT 1 lookup table

LD PLUT 1 lookup table plot

Original Mammogram

Figure 6b Resultant image after HD PLUT 1

Figure 6c Resultant image after conversion to grayscale

Grayscale gradient

Gradient after HD PLUT 1

Gradient after conversion to grayscale

HD PLUT 1 lookup table

HD PLUT 1 lookup table plot

Original Mammogram

Resultant
image after MC PLUT 1

Resultant image
close up after conversion
to grayscale

Grayscale gradient

Gradient after MC PLUT 1

Figure 7f Gradient
after conversion to grayscale

MC PLUT 1 lookup table

MC PLUT 1 lookup table plot

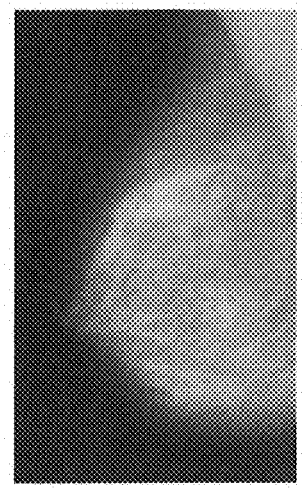
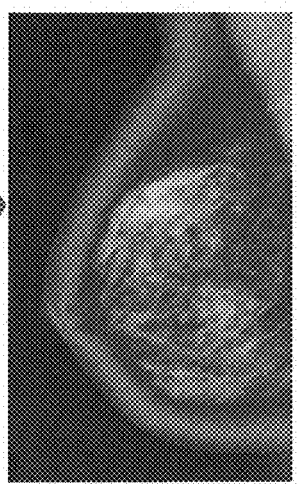
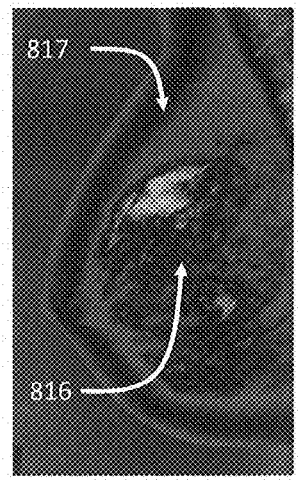
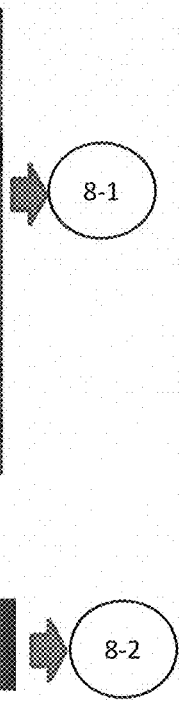
Figure 8a
Original Mammogram
Figure 8b
Resultant
image after RF PLUT 1
Figure 8c
Resultant
image after RF PLUT 2
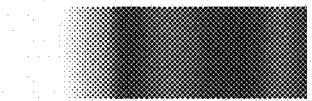
Figure 8d
Grayscale gradient
Figure 8e
Gradient after RF PLUT 1
Figure 8f
Gradient after RF PLUT 2
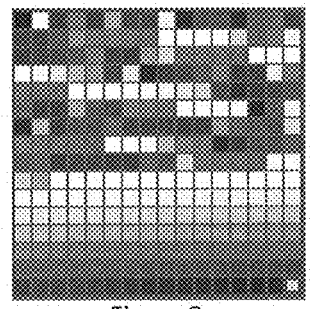
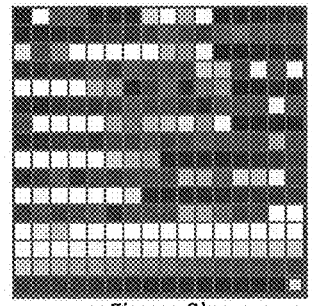
Figure 8g
RF PLUT 1 lookup table
Figure 8h
RF PLUT 2 lookup table
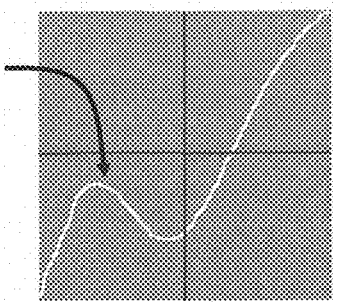
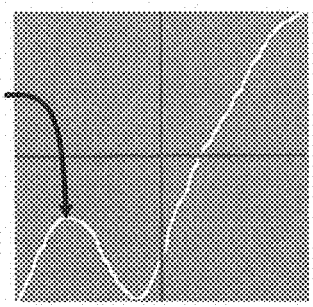
Figure 8i RF PLUT 1
lookup table plot
Figure 8j RF PLUT 2
lookup table plot

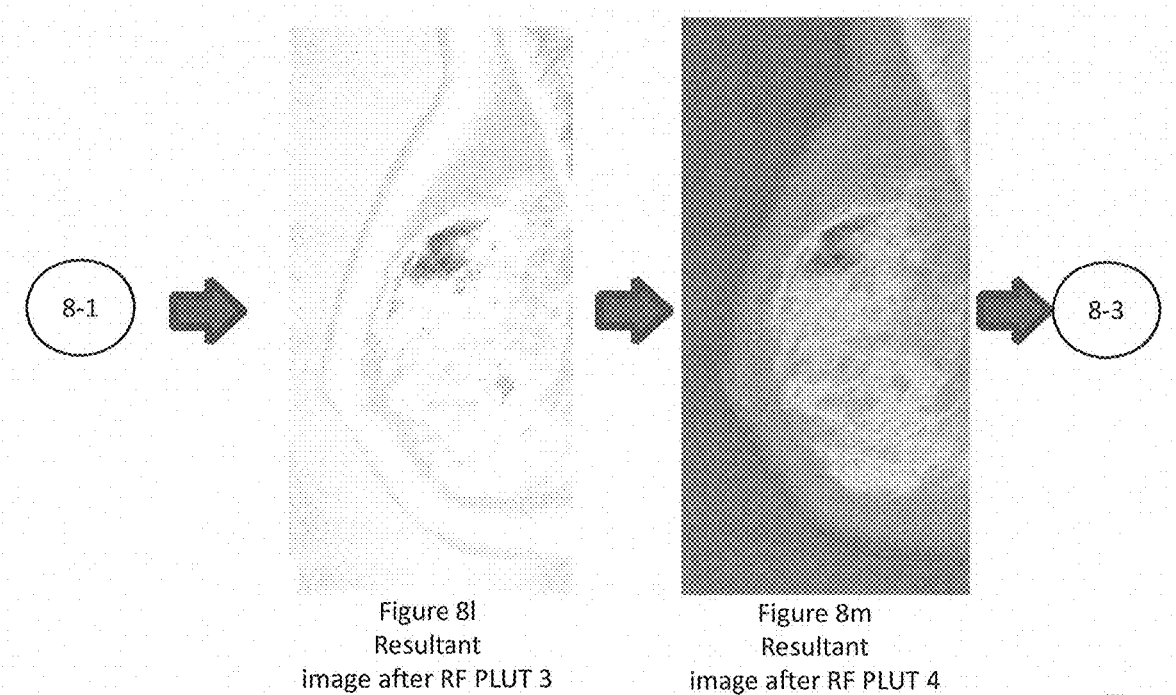
Figure 8l
Resultant
image after RF PLUT 3
Figure 8m
Resultant
image after RF PLUT 4
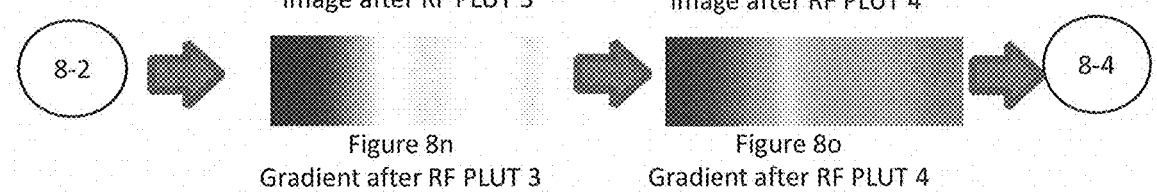
Figure 8n
Gradient after RF PLUT 3
Figure 8o
Gradient after RF PLUT 4
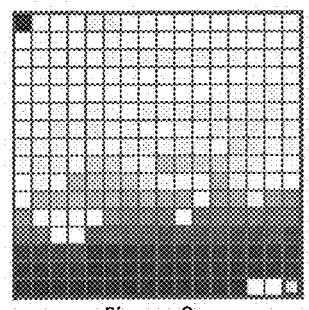 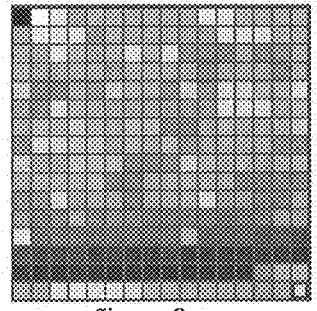
Figure 8p
RF PLUT 3 lookup table
Figure 8q
RF PLUT 4 lookup table
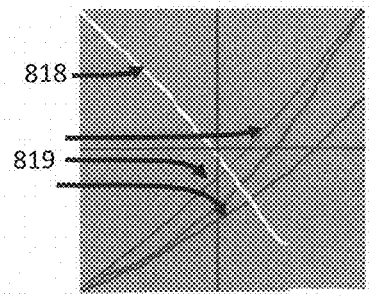 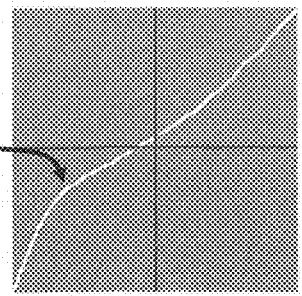
Figure 8k
RF PLUT 3 lookup table plot
Figure 8r
RF PLUT 4 lookup table plot Figure 8s Resultant
image after RF blend and grayscale conversion Gradient after RF blend and grayscale conversion

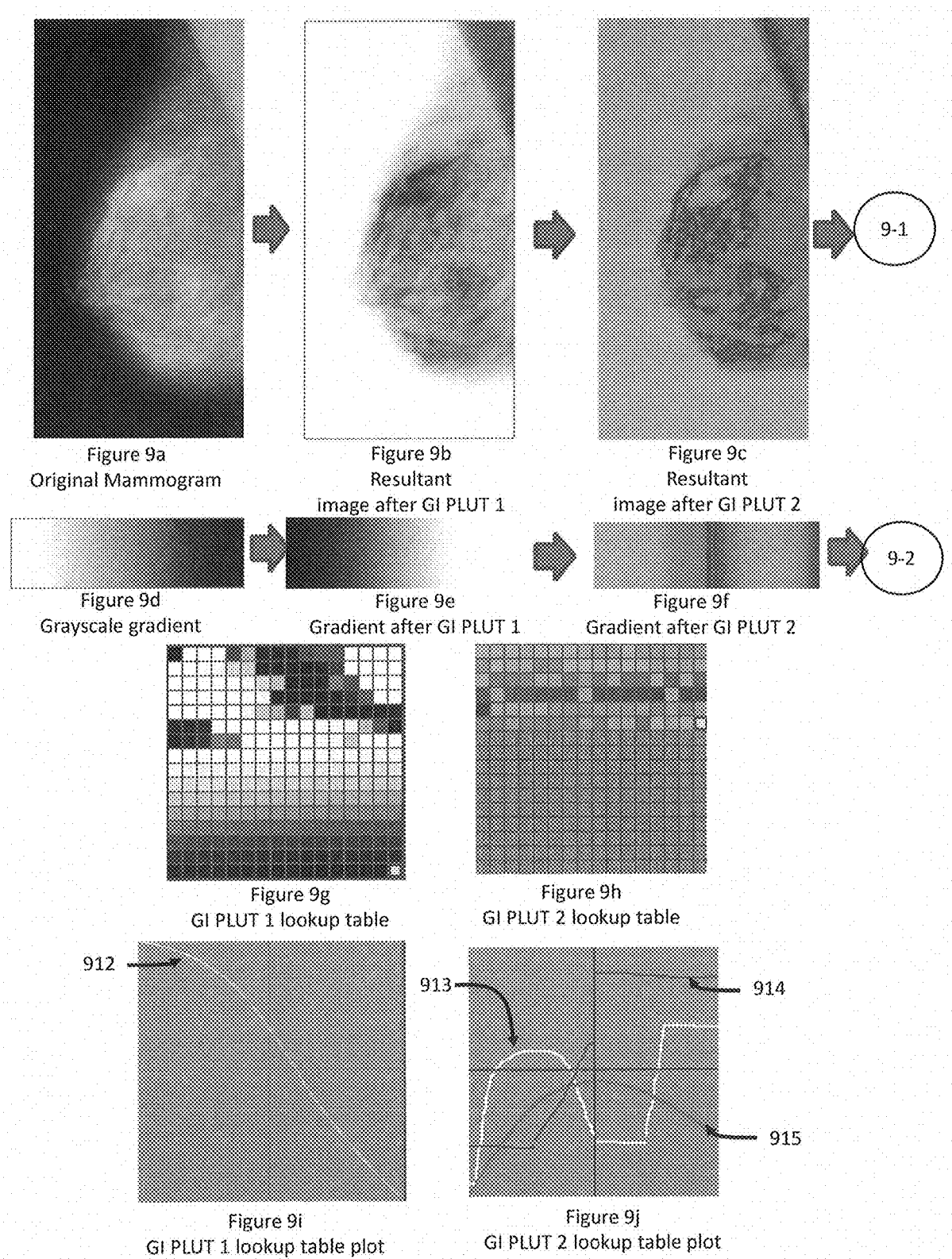

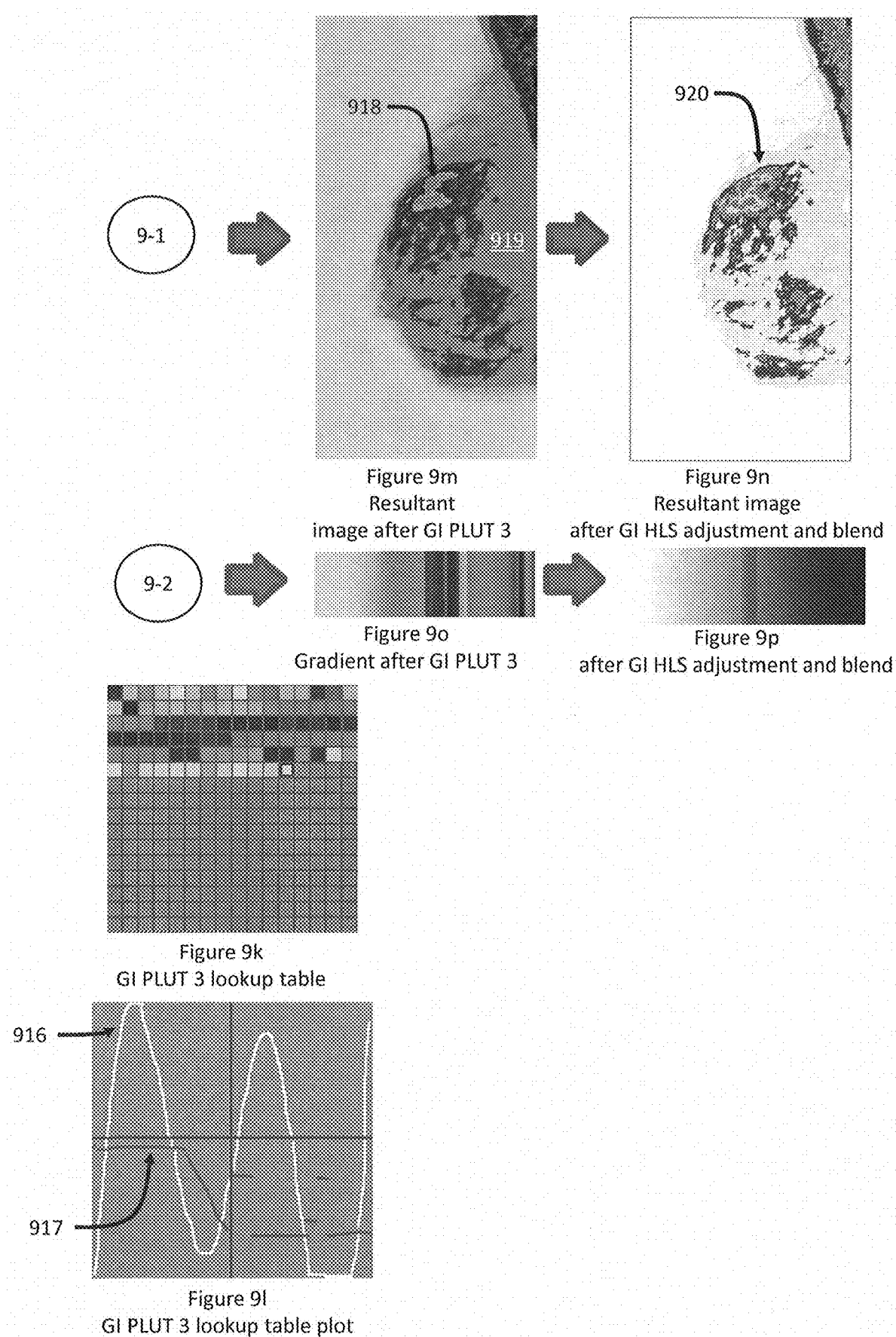

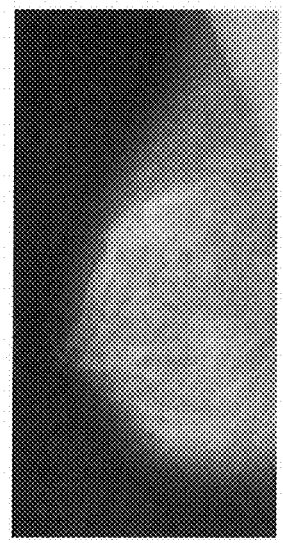
Figure 10a
Original Mammogram
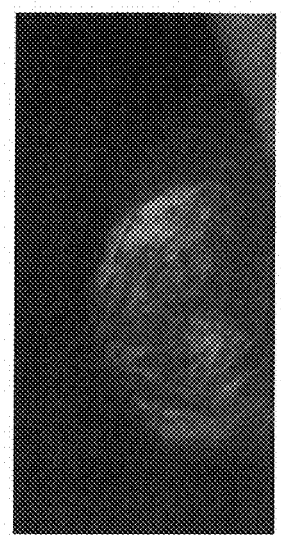
Figure 10b
Resultant image after RB PLUT 1
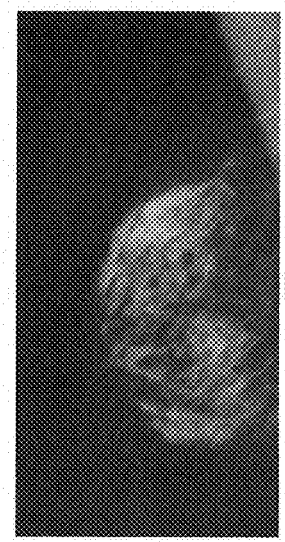
Figure 10c
Resultant image after RB PLUT 2
Figure 10d
Grayscale gradient
Figure 10e
Gradient after RB PLUT 1
Figure 10f
Gradient after RB PLUT 2
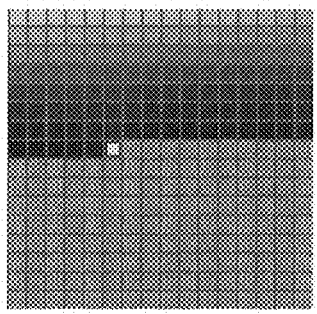
Figure 10g
RB PLUT 1 lookup table
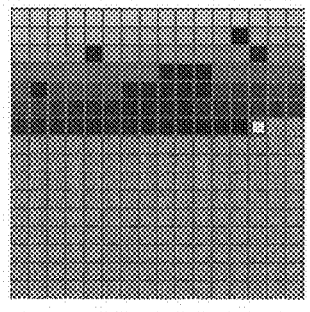
Figure 10h
RB PLUT 2 lookup table
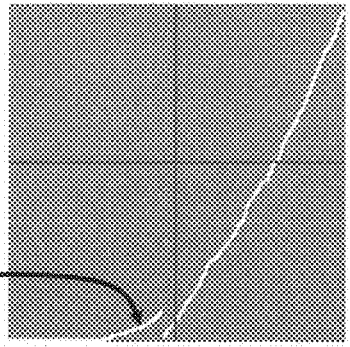
Figure 10i
RB PLUT 1 lookup table plot
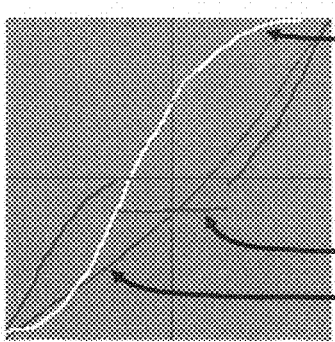
Figure 10j
RB PLUT 2 lookup table plot

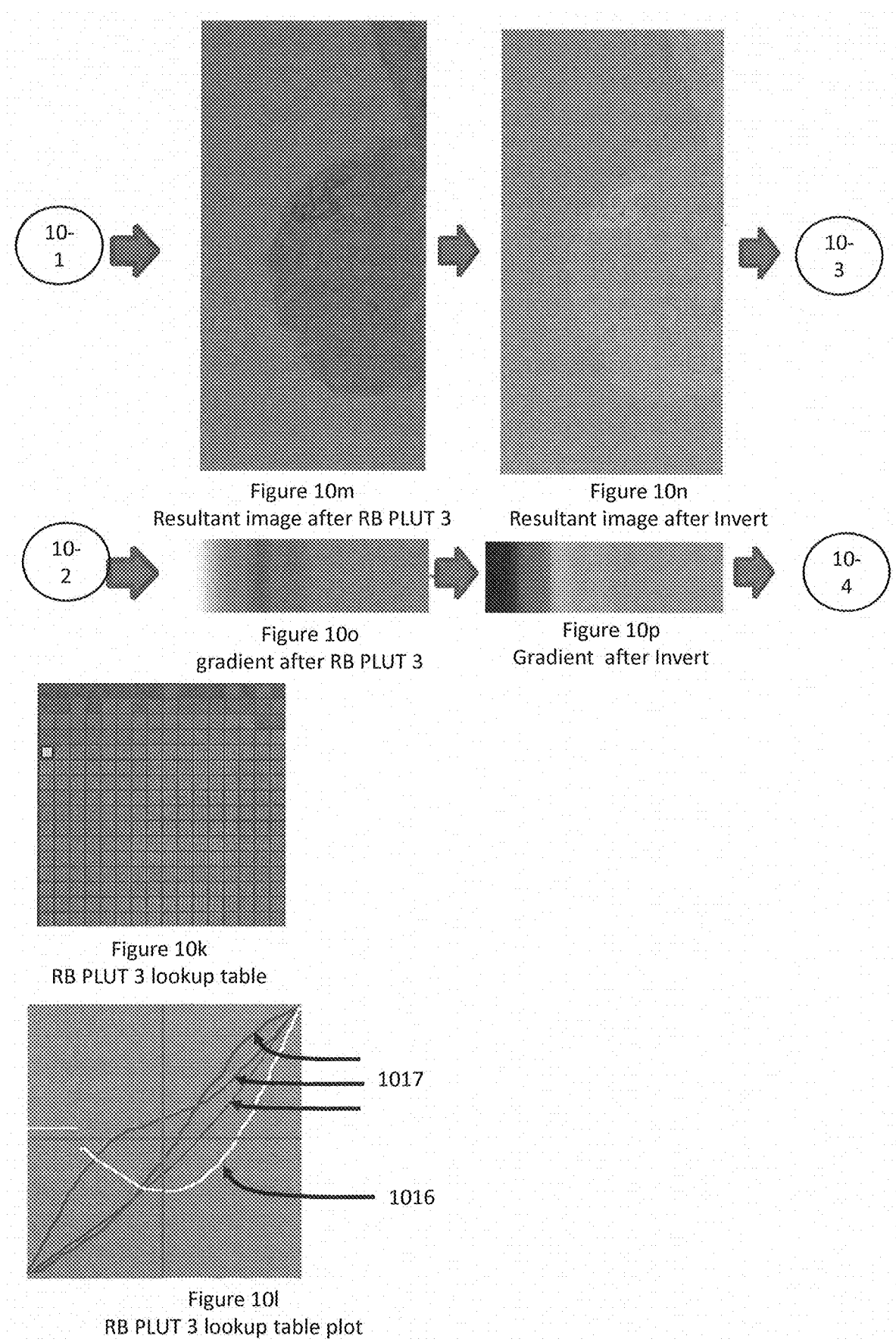

Resultant image after RB PLUT 4

Image after HLS adjustment

Figure 10u Gradient after RB PLUT 4

Gradient after HLS adjustment

RB PLUT 4 lookup table

RB PLUT 4 lookup table plot

SYSTEM AND METHOD FOR THE VISUALIZATION AND CHARACTERIZATION OF OBJECTS IN IMAGES

CROSS-REFERENCE TO RELATED APPLICATIONS

This application is a continuation of U.S. patent application Ser. No. 15/533,451 filed Jun. 6, 2017, which is a U.S. National Phase Application under 35 U.S.C. 371 of International Application No. PCT/US2017/016999 filed Feb. 8, 2017, which international application claims the benefit of U.S. Provisional Application No. 62/292,413 filed Feb. 8, 2016, all of which are incorporated herein by reference in their entireties.

BACKGROUND

The present invention generally relates to image processing and, more particularly, to a convergence-based system and method for the visualization and characterization of objects in images.

SUMMARY

In one embodiment there is a convergence-based method of visualizing and characterizing all features in a first grayscale image, such that the first image is duplicated into at least two channels with identical luminance values, then applying a local micro-contrast convergence algorithm that transforms at least some of the input values of each duplicate channel so that the output pixel values of each duplicate channel are different from both its input pixel values and those of every other duplicate channel's output pixel values, then using a look-up table to map values for each vector in each channel that, as a process, collectively produces a second image that is different from the first image.

Channels can be created as grayscale, alpha, color information channels, or a combination of the three.

In a further embodiment, applying a second local micro-contrast convergence algorithm, separate and distinct from the first local micro-contrast convergence algorithm, to the second image to produce a third image that is separate and distinct from the first image and separate and distinct from the second image.

In a further embodiment, altering the third image by sequentially applying one or more additional local micro-contrast convergence algorithms to generate a fourth image.

In a further embodiment, combining one or more of the first, second, third or fourth images to produce a fifth image that is separate and distinct from the first, second, third or fourth images.

In a further embodiment, a local micro-contrast convergence algorithmic sequence includes one or more of the preceding types of multi-dimensional (multi-channel) image transformations.

In a further embodiment, multi-dimensional image transformations may be expressed as a profile look-up table (PLUT) in a digital file format as hexadecimal code or text.

In a further embodiment, multi-dimensional image transformations may be stored as a PLUT in a digital file format as one or more matrices.

In a further embodiment, local micro-contrast convergence algorithms define and can process a sequence of transformations utilizing metrics specified in PLUTs that translate image input pixel values representing specific material types to image output pixel values to cause relationships among neighboring pixel groups to aggregate into predictable color and luminosity patterns consistent with the material's structure and relationship to its imaging modality; each material is uniquely characterized and can be visually differentiated.

In a further embodiment, local micro-contrast convergence, multi-dimensional image transformations may be stored as a PLUT in a digital file format where a set of two-dimensional input functions $F_1(x,y,i)$, $F_2(x,y,i)$ ..., $F_N(x,y,i)$ is mapped to a set of two-dimensional output functions $G_1(x,y,i)$, $G_2(x,y,i)$ ..., $G_N(x,y,i)$ with space variables (x, y) and luminance variable (i).

In a further embodiment, multi-dimensional image transformations may be stored as a PLUT in a digital file format where a set of two-dimensional input functions $F_1(x,y,i)$, $F_2(x,y,i)$ ..., $F_N(x,y,i)$ is mapped to a set of more than two-dimensional output functions in the form of sub-matrices $G_1(x,y,i,j,k,l)$, $G_2(x,y,i,j,k,l)$ ..., $G_N(x,y,i,j,k,l)$ with space variables (x,y), a luminance variable (i), and alpha or color channels (j,k,l).

In a further embodiment, a first grayscale image may be replicated into a first multi-dimensional space where each layer dimension of the multi-dimensional space is a replicate of the first image.

In a further embodiment, the number of dimensions in a multi-dimensional space equals two or more.

In a further embodiment, the number of dimensions in a multi-dimensional space equals four including luminance and the color components red, green, and blue.

In a further embodiment, the number of dimensions in a multi-dimensional space equals N dimensions of color spaces such as hue, saturation and lightness (HSL), CIE XYZ or CIELAB (The CIELAB color space, also known as CIE L*a*b* or sometimes abbreviated as simply "Lab" color space is a color space defined by the International Commission on Illumination, CIE, which expresses color as three numerical values, L* for the lightness and a* and b* for the green-red and blue-yellow color components), and CMYK (combination of Cyan, Magenta, Yellow, and Black colors).

In a further embodiment, converting a multi-dimensional color space image that was created by a local micro-contrast convergence algorithmic sequence into a single channel [dimension] grayscale image.

In a further embodiment, converting a multi-dimensional color space image into a single channel grayscale image by differentially altering the luminance values of colors in the first image as they are expressed in the grayscale (desaturated) image.

In a further embodiment, the functions utilized within a local micro-contrast convergence algorithmic sequence can include superposition additive or differential operators utilizing two or more resultant images from two different local micro-contrast algorithmic sequences.

In a further embodiment, one or more local micro-contrast convergence algorithmic sequences may employ finite area convolution filters with an M×M impulse response array for either sharpening or reducing noise in an image.

In a further embodiment, the resulting features that are visualized and characterized can be expressed in the context of a given first grayscale image wherein each object or material type converges to similar patterns or colors characteristic of its type, thereby expressing unique characteristics in response to the algorithmic sequence.

In a further embodiment, different local micro-contrast convergence algorithmic sequences can be utilized for the same given first grayscale image to express different convergent visualizations and characterizations of materials within that image by causing all like materials to converge into similar patterns or colors.

In a further embodiment, different algorithmic sequences may be created and applied to optimize the characterization of distinct material properties in an image, such as object boundaries, textures, fine structures, and changes within objects.

In a further embodiment, the first image is an image generated by x-ray, ultrasound, infra-red, ultra-violet, magnetic resonance imaging (MM), computed tomography (CT) scans, positron emission tomography (PET) scans, grayscale, color, visible light, millimeter wave, or laser scan.

In a further embodiment, a cancer, cyst or any abnormality of the breast tissue the breast, prostate, kidney, liver, bone, lung, brain, or skin of either a human or animal can be visualized and characterized within the context and patterns of all other structures in an image.

In a further embodiment, a biomarker for cardiovascular disease, Alzheimer's disease, diseases of the eye, or multiple sclerosis lesion can be visualized and characterized within the context and patterns of all other structures in the image.

In a further embodiment, a chemical marker for a solid or liquid organic compounds can be visualized and characterized within the context and patterns of all other structures in an image.

In a further embodiment, a structural defect or anomaly can be visualized and characterized within the context and patterns of all other structures in an image.

In one embodiment, there is a system of reducing the false positive error rate for visually or digitally expressing the presence of a feature in an image according to any of the methods described herein.

In one embodiment, there is a method of reducing the false negative error rate for visually or digitally expressing the presence of a feature in an image comprising: applying a local micro-contrast tissue convergence algorithm to a first image to produce a second image that is different from the first image.

In a further embodiment, the first image is an image generated by x-ray, ultrasound, infra-red, ultra-violet, MRI, CT scans, PET scans, grayscale, color, visible light, millimeter wave, or laser scan.

In a further embodiment, a cancer, cyst or any abnormality of the breast tissue the breast, prostate, kidney, liver, bone, lung, brain, or skin of either a human or animal can be visualized and characterized within the context and patterns of all other structures in an image.

In a further embodiment, a biomarker for cardiovascular disease, Alzheimer's disease, diseases of the eye, or multiple sclerosis lesion can be visualized and characterized within the context and patterns of all other structures in the image.

In a further embodiment, a chemical marker for a solid or liquid organic compounds can be visualized and characterized within the context and patterns of all other structures in an image.

In a further embodiment, a structural defect or anomaly can be visualized and characterized within the context and patterns of all other structures in an image.

In a further embodiment, the false negative rate for breast cancer detected or visualized by a radiologist in the second (i.e., subsequent) image is less than 16% for normal breasts and less than 60% for breasts having a portion of dense tissue.

In one embodiment, there is a system of reducing the false negative error rate of detecting or revealing a feature in an image according to any of the methods described herein.

In one embodiment there is a system comprising: one or more memory units each operable to store at least one program; and at least one processor communicatively coupled to the one or more memory units, in which the at least one program, when executed by the at least one processor, causes the at least one processor to perform the steps of: receiving an image; mapping pixel values of the image to an initial multi-dimensional color space; applying one or more local micro-contrast convergence transfer functions to the image's initial multi-dimensional color space to cause local micro-contrast convergence and to create a processed image with a multi-dimensional color space; and displaying that image visualization based on the processed multi-dimensional color space.

In a further embodiment, converting the processed multi-dimensional color space image to a single channel grayscale image.

In a further embodiment, the multi-dimensional color space image includes a luminance dimension having luminance values.

In a further embodiment, converting the processed multi-dimensional color space to a single channel grayscale image by differentially altering the luminance values of colors in the first image as they are expressed in the grayscale (desaturated) image for purposes of image display or analysis.

In a further embodiment, the multi-dimensional color space is an RGB color space.

In some embodiments, the multi-dimensional color space may be one of: HSV, HLS, HSB, XYZ, CMYK, CIEXYZ or CIELAB.

In a further embodiment, the system further comprising the processing of a breast image (mammogram, CT, MRI, or ultrasound): applying a median filter to the initial multi-dimensional color space; and wherein applying the one or more PLUTs to the initial multi-dimensional color space includes: applying a first set of PLUT functions to attenuate low density fatty breast tissue; applying a second set of PLUT functions to cause fatty breast tissue to appear as a first color and to differentiate the denser breast tissue using other colors; applying a third set of PLUT functions to amplify low pixel values and attenuate high pixel values in the color space layer associated with the first color; and applying a fourth set of PLUT functions to change the background of the image, when displayed, to black or other desired luminance or color value.

In a further embodiment, the system further comprising: receiving a second image, the second image being substantially similar to the first image; mapping pixel values of the second image to a second initial multi-dimensional color space; applying a median filter and a convolution filter to the initial multi-dimensional color space to create a second processed multi-dimensional color space; and displaying an image visualization based on the processed multi-dimensional color space associated with the first image and the second processed multi-dimensional color space associated with the second image, and wherein the applying the one or more PLUT functions to the initial multi-dimensional color space associated with the first image includes: applying a first set of PLUT functions to elevate darker values of the image and attenuate mid tones; applying a second set of PLUT functions to the multi-dimensional color space to add subtle color hues; and applying a third set of PLUT functions to expand the tonal values associated with cancer.

In a further embodiment, the system further comprising: adjusting gamma levels of the multi-dimensional color space to adjust the contrast of the first image and highlight structural details, and wherein the applying the one or more PLUT functions to the initial multi-dimensional color space associated with the first image includes: applying a first set of PLUT functions to diminish the luminance levels slightly; and applying a second set of PLUT functions to invert values of the initial multi-dimensional color space associated with luminance.

In a further embodiment, the first image is a mammogram that includes dense tissue and fatty tissue, and applying a first local micro-contrast convergence algorithm to a first image to produce a second image that is separate and distinct from the first image includes: mapping pixel values of the first image to a first multi-dimensional color space; applying a median filter to the first multi-dimensional color space to produce a second multi-dimensional color space; inverting the second multi-dimensional color space to produce a third multi-dimensional color space; applying a first set of one or more non-linear transfer functions to the third multi-dimensional color space to produce a fourth multi-dimensional color space and to cause fatty breast tissue to appear as one color and to differentiate the denser breast tissue using other colors; applying a second set of one or more transfer functions to the fourth multi-dimensional color space to produce a fifth multi-dimensional color space and to amplify high pixel values and attenuate low pixel values and to highlight the breast area structures; and displaying an image visualization based on the fifth multi-dimensional color space.

In a further embodiment, the first image is a mammogram that includes dense tissue and fatty tissue, and applying a first local micro-contrast convergence algorithm to a first image to produce a second image that is separate and distinct from the first image includes: mapping pixel values of the first image to a first multi-dimensional color space; applying a first set of one or more transfer functions to the first multi-dimensional color space to produce a second multi-dimensional color space and to cause fatty breast tissue to appear as one color and to differentiate the denser breast tissue using other colors; converting the second multi-dimensional color space to a third multi-dimensional color space in an HLS color space; and displaying an image visualization based on the third multi-dimensional color space.

In a further embodiment, the first image is a mammogram that includes dense tissue and fatty tissue, and applying a first local micro-contrast convergence algorithm to a first image to produce a second image that is separate and distinct from the first image includes: mapping pixel values of the first image to a first multi-dimensional color space; applying a first set of one or more transfer functions to the first multi-dimensional color space to produce a second multi-dimensional color space and to cause fatty breast tissue to appear as one color and to differentiate and reveal detailed structures in the denser breast tissue using other colors; and displaying an image visualization based on the second multi-dimensional color space.

In a further embodiment, the first image is a mammogram that includes dense tissue and fatty tissue, and applying a first local micro-contrast convergence algorithm to a first image to produce a second image that is separate and distinct from the first image includes: mapping pixel values of the first image to a first multi-dimensional color space; applying a first set of one or more transfer functions to the first multi-dimensional color space to produce a second multi-dimensional color space and to cause fatty breast tissue to appear translucent and to differentiate denser breast tissue using other colors, and to distinguish small dot-like structures; and displaying an image visualization based on the second multi-dimensional color space.

In a further embodiment, the first image is a mammogram that includes dense tissue and fatty tissue, and applying a first local micro-contrast convergence algorithm to a first image to produce a second image that is separate and distinct from the first image includes: mapping pixel values of the first image to a first multi-dimensional color space; applying median filter to the first multi-dimensional color space to produce a second multi-dimensional color space; applying a convolution filter to the second multi-dimensional color space to produce a third multi-dimensional color space; importing a duplicate first image; mapping image pixel values to a fourth multi-dimensional color space; applying a first set of one or more transfer functions to the fourth multi-dimensional color space to produce a fifth multi-dimensional color space and to build contrast and darken fatty tissue; applying a second set of one or more transfer functions to the fifth multi-dimensional color space to produce a sixth multi-dimensional color space and to build contrast and darken fatty tissue; applying a third set of one or more transfer functions to the sixth multi-dimensional color space to produce a seventh multi-dimensional color space and to invert fatty breast tissue luminance to appear as one color and to differentiate and reveal detailed structures in the denser breast tissue using other colors; applying a fourth set of one or more transfer functions to the seventh multi-dimensional color space to produce an eighth multi-dimensional color space and to define the breast boundary; merging the third multi-dimensional color space with the eighth multi-dimensional color space to produce a ninth multi-dimensional color space; converting the ninth multi-dimensional color space to grayscale values and displaying an image representative of the ninth multi-dimensional color space.

In a further embodiment, the first image is a mammogram that includes dense tissue and fatty tissue, and wherein applying a first local micro-contrast convergence algorithm to a first image to produce a second image that is separate and distinct from the first image includes: mapping pixel values of the first image to a first multi-dimensional color space; applying a first set of one or more transfer functions to the first multi-dimensional color space to produce a second multi-dimensional color space and to cause the image pixel values to invert non-linearly; applying a second set of one or more transfer functions to the second multi-dimensional color space to produce a third multi-dimensional color space and to cause fatty breast tissue to appear as one color and to differentiate and reveal detailed structures in the denser breast tissue using other colors; applying a third set of one or more transfer functions to the third multi-dimensional color space to produce a fourth multi-dimensional color space and to cause fatty breast tissue to appear as one color and to differentiate and reveal detailed structures in denser breast tissue using other colors; converting the fourth multi-dimensional color space to a fifth multi-dimensional color space in an HLS color space; merging the fifth multi-dimensional color space with the first multi-dimensional color space by employing a darken blend to produce a sixth multi-dimensional color space; adjusting the opacity of the sixth multi-dimensional color space to produce a seventh multi-dimensional color space; and converting the seventh multi-dimensional color space to grayscale values and displaying an image representative of the seventh multi-dimensional color space.

In a further embodiment, the first image is a mammogram that includes dense tissue and fatty tissue, and wherein applying a first local micro-contrast convergence algorithm to a first image to produce a second image that is separate and distinct from the first image includes: mapping pixel values of the first image to a first multi-dimensional color space; applying median filter to the first multi-dimensional color space to produce a second multi-dimensional color space; applying a first set of one or more transfer functions to the second multi-dimensional color space to produce a third multi-dimensional color space and to alter the contrast and reduce luminosity of fatty tissue; applying a second set of one or more transfer functions to the third multi-dimensional color space to produce a fourth multi-dimensional color space and to colorize all breast tissue except those of the higher density; applying a third set of one or more transfer functions to the fourth multi-dimensional color space to produce a fifth multidimensional color space and to reduce the fatty tissue to an almost solid color; inverting the colors of the fifth multi-dimensional color space to produce a sixth multi-dimensional color space; applying a fourth set of one or more transfer functions to the sixth multi-dimensional color space to produce a seventh multi-dimensional color space and to differentiate the breast from outside its boundary; converting a seventh multi-dimensional color space to an eighth multi-dimensional color space in an HLS color space and adjust HLS properties of the eighth multi-dimensional color space to produce a ninth multi-dimensional color space; displaying an image visualization based on the ninth multi-dimensional color space.

In one embodiment, there is a method performed by the system described herein.

BRIEF DESCRIPTION OF THE SEVERAL VIEWS OF THE DRAWINGS

The foregoing summary, as well as the following detailed description of embodiments of the invention, will be better understood when read in conjunction with the appended drawings of an exemplary embodiment. It should be understood, however, that the invention is not limited to the precise arrangements and instrumentalities shown.

In the drawings:

FIGS. 4a to 4k show an exemplary local micro-contrast convergence algorithmic sequence to process mammographic images to reveal breast abnormalities in resultant color images according to at least some embodiments of the invention.

FIGS. 6a to 6i show an exemplary local micro-contrast convergence algorithmic sequence to process mammographic images to reveal details in dense breast tissues in resultant grayscale images according to at least some embodiments of the invention.

FIGS. 7a to 7j show an exemplary local micro-contrast convergence algorithmic sequence to process mammographic images to reveal the presence of microcalcifications in dense breast tissues in resultant grayscale images according to at least some embodiments of the invention.

FIGS. 9a to 9q shows an exemplary local micro-contrast convergence algorithmic sequence to process mammographic images to reveal breast abnormalities in resultant grayscale images according to at least some embodiments of the invention.

DETAILED DESCRIPTION

Figure 1A:
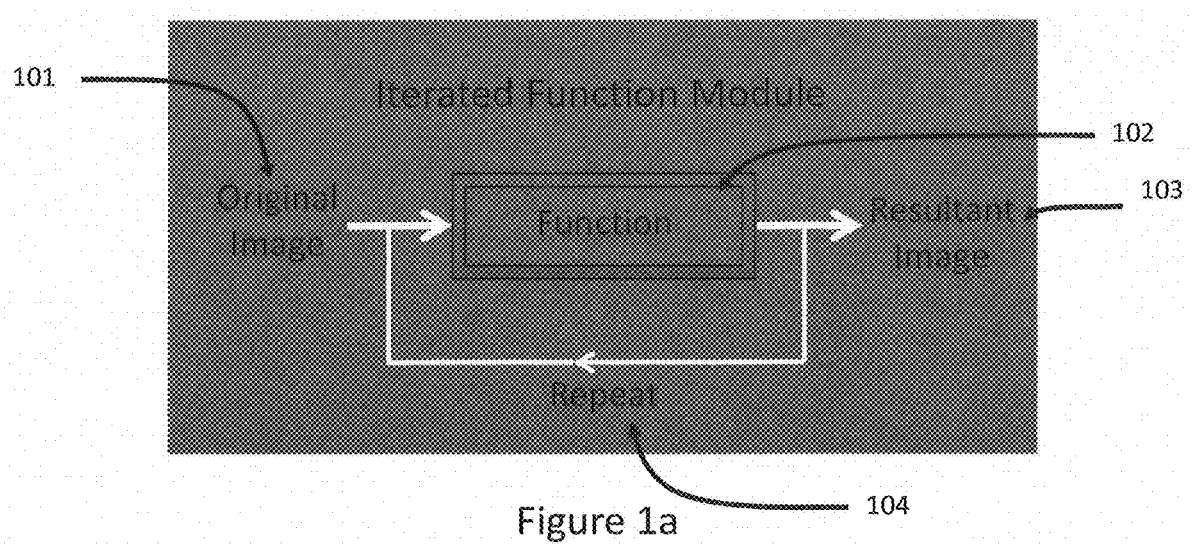
FIG. 1a is a diagram illustrating the elements of an Iterated Function Module in accordance with at least some embodiments of the invention.

Referring to the drawings in detail, wherein like reference numerals indicate like elements throughout, there is shown in FIGS. 1a-11h systems, devices and methods, generally designated, in accordance with exemplary embodiments of the present invention.

Introduction

Most image processing and analysis methodologies in medicine, for example, are designed to cause areas within an image to diverge, bifurcate, or be isolated as areas of interest (AOIs). In these processes, the AOIs become isolated by applying one or more sequences of segmentation algorithms. Many image processing and analysis methodologies, known as computer aided detection (CAD) processes, are designed to be used for identifying the presence of breast cancer in mammograms, other diseases in other modalities, and for applications outside of medicine. Results of studies have shown that, the CAD processes used in breast image analysis have false positive rates of up to 5,000 to 1. The false positive rate is the ratio between the number of negative events wrongly categorized as positive (false positives), and the total number of actual negative events.

It is the process of visual or data segmentation of objects of interest, the bifurcating of objects in an image, and/or the subsequent isolation from other tissues of the image (divergence), that greatly limits the effectiveness of such techniques to clinicians. Because bifurcating/segmenting processes remove the context of surrounding objects/tissues from any larger context in which the AOIs occur, the diagnostic value of such processes to doctors are greatly limited since the location of disease or abnormality within the breast and its surrounding tissues limits its use in making improved clinical decisions on possible outcomes and treatments.

Many mathematical approaches have been devised to examine original grayscale images by utilizing local properties within the image such as luminance values, running mean filters, rubber-band straightening transforms, measurements of circularity at a suspected region of interest, texture, gradient histogram, and gray level increment analysis. Many of these approaches fail to produce acceptable results in areas of the image where the objects to be detected are very similar to the values of the surrounding neighborhood values. A cancer may be detected, but its margins (boundaries) may not be clearly established. Still others, utilize machine learning where an atlas of known pathology is compared with an image being processed for determining a probability of likelihood based on similarities between the atlas and the unknown set of image metrics in the image being analyzed.

In addition, many CAD methodologies do not improve visualization and characterization of objects in the processed image as an aid to the radiologist to visually confirm the extent of the abnormalities or distinguish characteristics of abnormalities from normal tissue. Instead, CAD approaches simply place a location marker within an original mammogram image. This further provides a dilemma for a radiologist in that no additional discriminating visual information is available to assess the validity of the marker. Using CAD methodologies, the radiologist must not only assess the original image for the presence of cancer or other abnormalities, but also assess the validity of a given marker, while being aware of the very high false positive rate associated with the CAD process. Similar deficiencies exist in a broad spectrum of fields that use CAD methodologies or image segmentation algorithmic approaches.

Thus, there is a need in the art to improve image-processing techniques beyond those of CAD, bifurcating, or divergence-based processes.

Breast Cancer Imaging Domain Application

Mammography is the use of X-ray radiographs to generate an image of a person's breast to detect the possible presence of breast cancer or other abnormalities. While the use of mammograms is currently the best methodology available for screening to detect breast cancer, between 10% and 30% of women with cancer are reported as negative (i.e., cancer free). This may be due in part to the very complex, and often very subtle nature of detecting cancer in mammographic images, and is especially a serious issue for women with dense breast tissue who have a higher potential of getting breast cancer. Cancer in mammograms appears white, yet the breast contains non-cancerous elements that also appear white (e.g., dense breast tissue) and dark (e.g., fatty breast tissue). Radiologists more easily observe cancers in fatty tissue, yet cancers occurring in dense breast tissue are very difficult to distinguish from surrounding tissue. Almost 40% of women have breasts that contain at least a portion of dense tissue; consequently, there is a significant need to be able to distinguish cancerous lesions regardless of the level or relative amount of density in a woman's breast tissue.

Moreover, when a radiologist determines that breast cancer may be present in a mammogram several possible follow-up procedures may be employed. These may include the use of ultrasound, mammogram (MM) with contrast, breast CT scans, and biopsies. These follow-up procedures are expensive, are frequently emotionally traumatic to the patient and their family and, in some instances, can cause physical trauma. The positive predictive value of ultrasound, when indicating the need for a biopsy, is only 9%. Clinically, 91% of patients who have biopsies following ultrasound are confirmed by pathology as not having cancer. Similarly, 60% of patients having an MRI and going on to biopsy do not have cancer. As used herein, positive predictive values refer to the probability that subjects with a positive screening test have the disease. As used herein, negative predictive value refers to the probability that subjects with a negative screening test do not have the disease.

Ultrasound patients who have indications of possible disease in a mammogram may be sent to have an ultrasound or have an MM exam with contrast. When ultrasound is performed and a radiologist determines from the ultrasound image that a cancer might be present, a biopsy is often recommended. Of those patients that had a follow-up biopsy, based on an ultrasound, 91% did not have cancer.

An approach that can reveal cancer with a high degree of sensitivity and specificity, and utilizing only standard screening and inexpensive imaging (e.g., mammograms) will provide a breakthrough in today's cancer detection environment. Approximately 90% of breast cancers arise in the cells lining the ducts of breast tissue. Early detection of breast cancer relies on a clinical capability to distinguish such changes as might be present in an image. Again, the presence of local or general dense breast tissue makes this a very challenging task. As a function of breast density, dense breasts can be understood to include 5% to 95% dense breast tissue. Typically, densities vary throughout the breast volume with some local regions having greater or lesser density than other (e.g., different or nearby) regions. Overall, there may be specific regions in a woman's breast is very high density and other areas of very low density containing fatty tissue. In some women, the entire breast is extremely dense, while in others there are only spots where high density occurs. Regardless of the amount of density that is high as a percentage of a woman's breast, any cancer occurring within a high-density area is subject to being misdiagnosed because breast cancer appears white in a mammogram as does dense breast tissue often leading to a radiologist inability to discriminate between the high density and the cancer itself.

Breast cancer can develop from normal tissues in one or more different progressions of change. Abnormal tissue development may progress from being normal to Hyperplasia to Atypical Hyperplasia to ductal carcinoma in situ (DCIS) to invasive DCIS. Tissues can evolve from being normal to being an invasive carcinoma with no intervening steps. Once the tumor has grown beyond the duct, it is called an invasive carcinoma.

Currently, only 1% of breast cancers are capable of being detected when the lesion is 1 mm in size or less.

The challenges of using computer aided detection and machine-learning techniques to detect cancer in images showing local or general variation densities of tissue are compounded by the variability associated with the dynamic structure changes that can occur in living tissues. Segmentation of disease involving this number of possible combinations makes it very difficult to train computers to consistently detect cancer while maintaining a low number of false positives.

Techniques such as standard machine learning protocols, the use of segmentation algorithms, and processes for causing only pixels associated with disease to be isolated (i.e., segmented or bifurcated) in images have the issue of having too many combinations as possibilities to correctly identify the disease. These processes function best when there is a SINGLE object that has unique boundaries associated with the object of interest. For example, identifying bacteria in an image generated through a microscope is aided because bacteria have definite shapes and sizes and the cell boundaries limit other possible combinations. As the name implies, bifurcation of images results in abrupt changes that lead to binary (yes/no) results and does not allow for subtle differences at boundaries within a given domain of image content.

In contrast, breast cancer, as well as other diseases and abnormalities, has diffuse boundaries. The cancer is most often amorphous and multi-patterned. Tissues may also be in a variety of transition states. A lesion may have cells that are in the Atypical Hyperplasia state as well as being Ductal Carcinoma in Situ, and becoming invasive. Additionally, both normal and abnormal breast conditions may include or be affected by:

Presence of spiculations and calcifications
Presence of necrotic tissue
Abundance of dense fibroglandular tissue associated with embedded cancer
Prior surgeries, biopsies, or weight gain
Changes to a woman during her menstrual cycle or from menopause.

Conventional CAD Approaches

In general, radiographic findings related to breast cancer generally involve identifying the presence of two different types of structures, masses and microcalcifications.

Microcalcifications related to pathology generally occur in ducts and in association with neoplasms. Masses most often correlated with abnormalities and can either be benign or cancerous. Fibroglandular tissues within the breast can obscure masses, making detection difficult in unprocessed images.

In mammography, two mammographic views are generally created for each breast (cranial/caudal CC and medial lateral oblique MLO) to assure that all breast parenchyma are included in the views. This further complicates the task of cancer detection and quantification in that it is hard to correlate the presence and dimensionality of structures between the two different views.

Existing computerized diagnostic methodologies typically employ the following sequence of processing: Suspect lesion>lesion extraction>feature extraction>classification>Predict probability of malignancy>report probability.

In these methodologies, it is important to segment or extract (e.g., cause to divide) areas of concern to be able to analyze the areas for possible malignancy. For example, applying equalization or divergence processes to the image differentiate fatty from more dense tissue. The equalization process is limited in that it is a linear process and has no specific thresholding that is optimal for all mammograms. While divergence-type segmentation algorithms may be used in separating fatty from dense tissue, it does not effectively support differentiation of white cancer areas within white dense breast tissue.

Binary processes are typically designed to look for specific diseases, but do not address other diagnostically important features in mammographic or other medical images such as architectural distortions of the breast, degree of asymmetry between breasts, nipple retractions, dilated ducts, and skin lesions. While not being cancerous, these features are still of importance to the clinician and their patients. While segmentation and bifurcating divergence algorithmic approaches focus on cancer, they are not designed to address the overall structures of all tissues in the image.

These segmentation techniques often use analysis of gray level increments in pixels, to define the boundaries of a possible lesion. Other techniques use probabilistic interpolation of pixel data but the interpolation method is limited again by the extreme similarities between lesions and dense tissue.

Local Micro-Contrast-Based Convergence

In some embodiments of the invention, there are disclosed systems and methods associated with image processing methodologies designed to improve visualization and maintain context of all tissues by differentially and predictably visualizing and characterizing all structures and features within the context of a given image. These embodiments employ a process of iterative sequencing of image processing functions that cause the local micro-contrast patterns associated with each material type to coalesce (or converge) and consistently be expressed as distinctive characteristic patterns within the resulting processed image. In other words, these embodiments provide an approach for the characterization of all tissue types within the context of the rest of the tissues, rather than attempting to extract or remove identified tissue types outside the context of the rest of the tissues.

Many objects in the real world, such as biological growth, patterns of neurons, branching of rivers, corrosion of pipes, and formation of snowflakes, are statistically self-similar where the patterns of development show the same statistical properties at many scales of magnification. In these patterns, a small piece of the object or pattern is similar to the patterns at a larger scale. These self-similar natural patterns are expressed as discrete pixel neighborhoods captured in images. An iterative process that may be used in the local micro-contrast convergence methodology, as utilized in at least some embodiments of the invention described herein, is designed to, and functions in a way, that explicitly visualizes and characterizes these self-similar patterns at any scale in the image.

FIG. 1a shows one embodiment of the local micro-contrast convergence algorithmic sequence pathway approach. An original image 101, e.g., a grayscale image 101, is input into the Iterated Functional Module processing sequence. The image 101 is then processed by an image processing function 102 which either becomes the resultant image 103 or is further processed by applying a second, but different image processing function at function 102. The repeating process 104 may be applied from 0 to n times.

Diseases such as cancer exhibit such self-similarity in its growth, and that growth can be characterized and visualized at any scale utilizing the local micro-contrast process where very small cancerous lesions exhibit the same expressed patterns as large lesions.

While fractal geometry can generate patterns of nature through the iteration of mathematical functions, the approach exemplified in this set of embodiments mathematically decomposes the fractal patterns generated in biological systems into identifiable and measurable expressions of pixel data within an image. Consequently, the local micro-contrast convergence algorithms described herein can be mathematically parallel to an iterative process, and can visualize tissue patterns such as breast boundaries, cancerous and benign lesion margins and cores, and characteristics of breast asymmetry that can be present in mammographic images.

As used herein, local micro-contrast convergence may refer to an iterative sequencing of image transformations utilizing profile look-up table (PLUT) functions.

As used herein, the PLUT functions refers to mathematical expressions in a matrix/array that specifies image input and output values of an image so that localized, self-similar image contrast pixel variables (such as statistically-based co-occurrence of pixel neighborhood relationships—textures for example) in the source image, have a discrete sets of values (called reconstruction levels) where the pixels in each local neighborhood (e.g., pixels having similar characteristics) in the source image are assigned a single color or luminance value in a resulting output image.

Singular or iterative applications of PLUT and other functions in the local micro-contrast convergence process can cause relationships among neighboring pixel groups to converge or aggregate into repeatable and predictable color and/or luminosity patterns consistent with the material's structure and relationship to its imaging modality. Although tissue/material types may vary significantly, each tissue/material type possesses common underlying pixel neighborhood relationships. The resulting local micro-contrast convergence patterns expressed in each area of the image are capable of visually expressing their characteristic color patterns based on e.g., the statistically-based distribution of luminance values for each object or material, regardless of the presence of surrounding and overlying materials of different types. For example, using a local micro-contract convergence algorithm, a breast cancer lesion in a mammogram can be characterized with a specific visually-observable and uniquely quantifiable pattern regardless if it is in dark fatty or high luminance dense breast tissue.

Figure 1B:
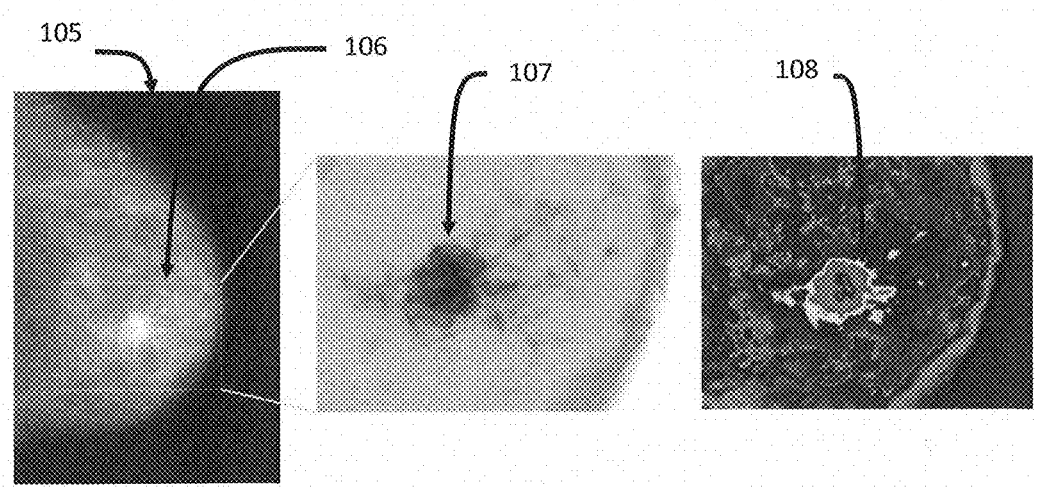
FIG. 1b shows two resultant image representations after processing an original mammogram with two different local micro-contrast convergence algorithmic sequences to reveal patterns of cancer in accordance with at least some embodiments of the invention.

FIG. 1b shows an original mammogram image 105 and two resultant images 107, 108 produced using at least some embodiments of the invention. A box outlining the area of cancer is shown at 106. Two resultant images are created by two different local micro-contrast convergence algorithmic sequences reveal distinctive patterns of the cancer as shown at 107 and 108. The iterative processing sequence transformed the subtle grayscale patterns of the original X-ray of the breast into characteristic pattern responses, such as edges, boundaries, internal structures, textures, spiculations, and luminance values and colors associated with a cancer response.

Figure 1C:
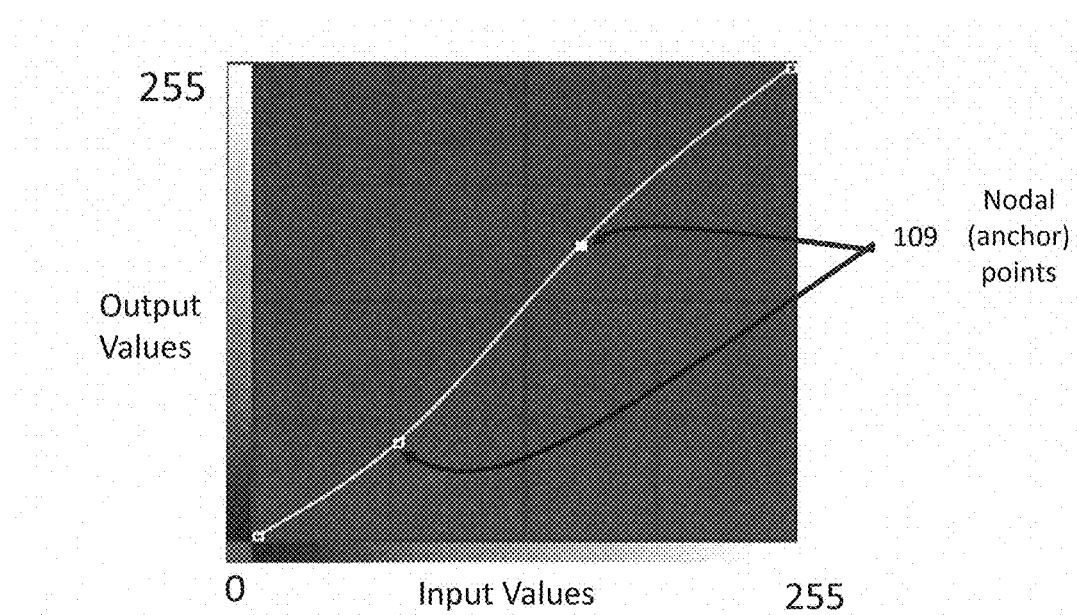
FIG. 1c shows a characteristic non-linear luminance transform "tone adjustment curve" with 2 nodal (anchor) points where the shape of the curve was adjusted to change the input to output values in accordance with at least some embodiments of the invention.

FIG. 1c illustrates a standard photographic coordinate system used to plot an image transformation using 2 nodal points at 109. As used herein, a nodal point refers to a singular point on a curve where the direction of the curve is altered. Moving any nodal point on a curve alters surrounding aspects of the curve. The input values of the original image are indicated along the bottom of the plot (x axis) and the output of the image values are indicated on the vertical axis. There are limitations with this approach. Nodal points change the shape of the "curve" and modify the relationship between the input values and the output values of an image. However, nodal points must be linked so that all parts of the curve are continuous. Therefore, it is limited to what can be mapped with continuous and linked values. Non-linear transformations utilizing nodal points perform poorly when separation of objects of nearly equal densities is desired.

Currently, feature extraction is completely dependent on the degree to which objects have successfully been segmented or extracted from the image's pixel data. While existing algorithms are optimally designed to locate the brightest area of a possible lesion, they often fail to distinguish the external boundaries of the lesion, an area important in diagnosis to determine where angiogenesis is occurring.

In this application, the one or more local micro-contrast convergence functions are without nodal points so that an image can be processed to properly define possible external boundaries of a legion (or other feature of interest).

Figure 1D:
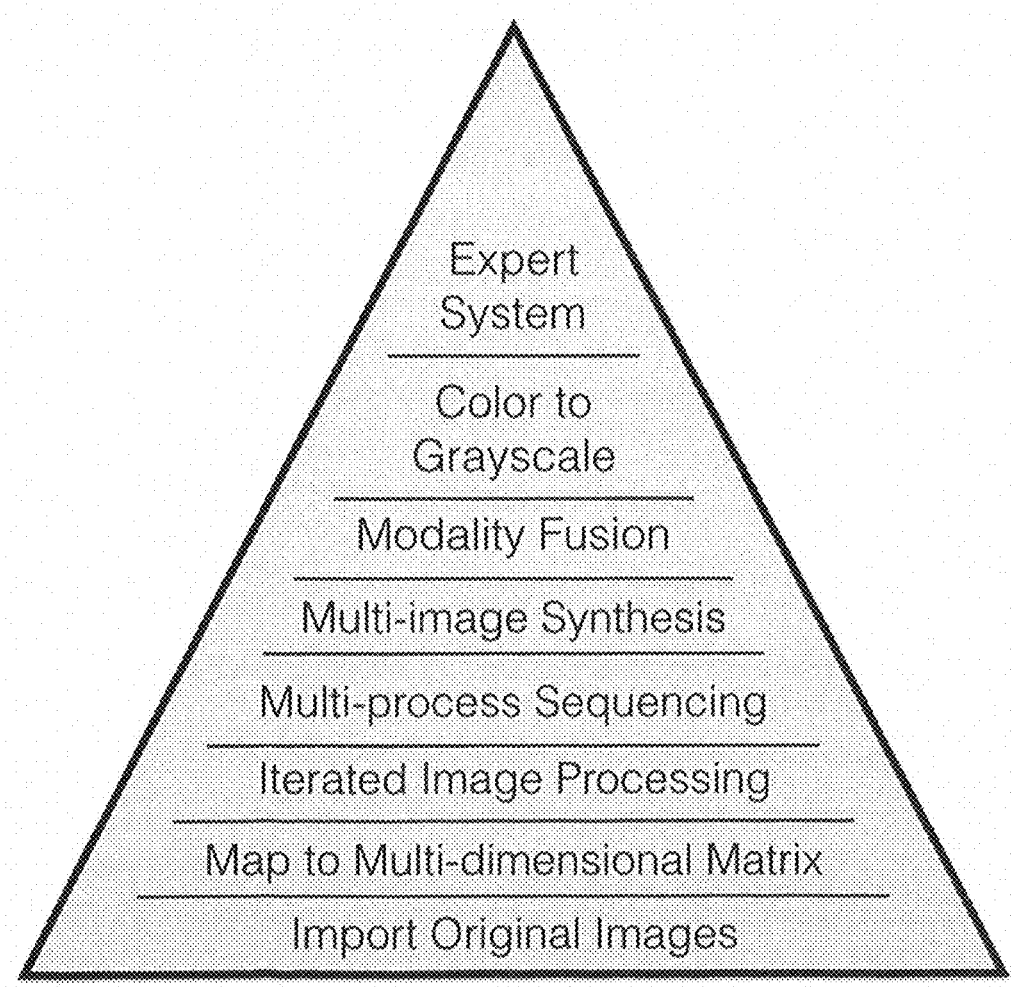
FIG. 1d shows the hierarchical structure of the levels of image processing and analysis embodied in accordance with at least some embodiments of the invention.

FIG. 1d diagrams the hierarchical approach to the implementation of the local micro-contrast convergence process. The sequence progresses from the bottom of the triangle to the top as it relates to higher levels of processing integration.

Multi image Modality Fusion is supported in the local micro-contrast convergence process. Modality Fusion, as it relates to the embodiment of this application, is a process of adapting the input values of images from different types of imaging modalities, so that the same, or slightly modified local micro-contrast convergence algorithmic sequences, can visualize and characterize, the same types of tissues between different imaging modalities. A local micro-contrast convergence pattern would then be similar for a patient's cancer when viewed in an X-ray, ultra-sound, breast CT, and MRI scan. This allows for combining information from different input modalities in a principled way. The imaging-based fusion approach facilitates early fusion, in which signals are integrated at the image feature level, and late fusion, in which information is integrated at the semantic level using post-processing image feature analytic tools.

These data can be used to generate one or more probability distribution functions correlated to localized response patterns at one or more vector coordinates to characterize materials such as normal, benign, and cancerous breast-tissue-types and correlate that data from a multiplicity of X-ray, MM, or ultrasound images, even when the tissues/materials are overlaid with other tissue/material types.

In some embodiments, the Multi-processing Sequencing, Multi-image Synthesis, and Modality Fusion, the resultant images can be analyzed, and data correlated among those images within an Expert System. Since all tissues are visualized in the local micro-contrast convergence process, diseases can both be detected and their pathology correlated to their occurrence within the organ of origin. This provides opportunities for advanced research in disease prevention and drug/treatment therapies.

At least some embodiments of the invention described herein are capable of consistently characterizing tissue/material types in images where other mathematical models, built on purely deterministic, or deterministic with simple random components fail, due to the complex stochastic non-Euclidean fractal-like shapes involving patterns of growth/development represented in images of natural processes like those in medicine.

In some embodiments, the methods are designed specifically to be able to identify structures within structures. For example, in medical imaging applications, the finalized images provide visual evidence as to the presence and structure of abnormal tissues in the context of the remaining structure in the image. The finalized images may also provide a mechanism to correlate abnormal objects to other normal and abnormal tissue types. For example, a cancerous lesion that is in a milk duct has a different level of concern than a lesion that has become invasive or appears to be associated with a lymph node. Similarly, a carcinoma in proximity to microcalcifications requires a different clinical interpretation as compared to a carcinoma next to the chest wall or in situations where there is significant asymmetry in the breast.

Figure 1E:
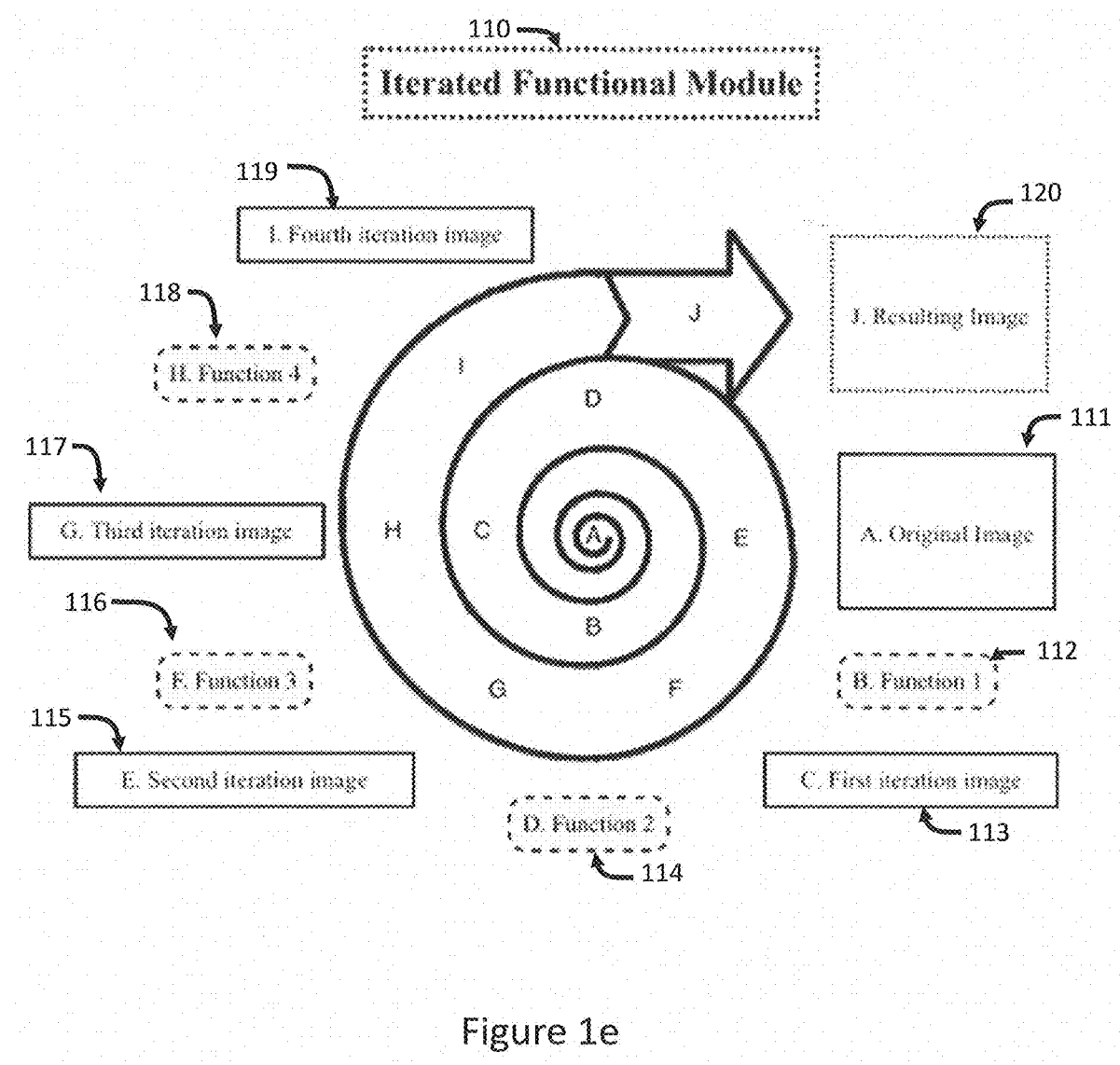
FIG. 1e shows a local micro-contrast convergence algorithm sequence according to at least some embodiments of the invention.
Figure 1F:
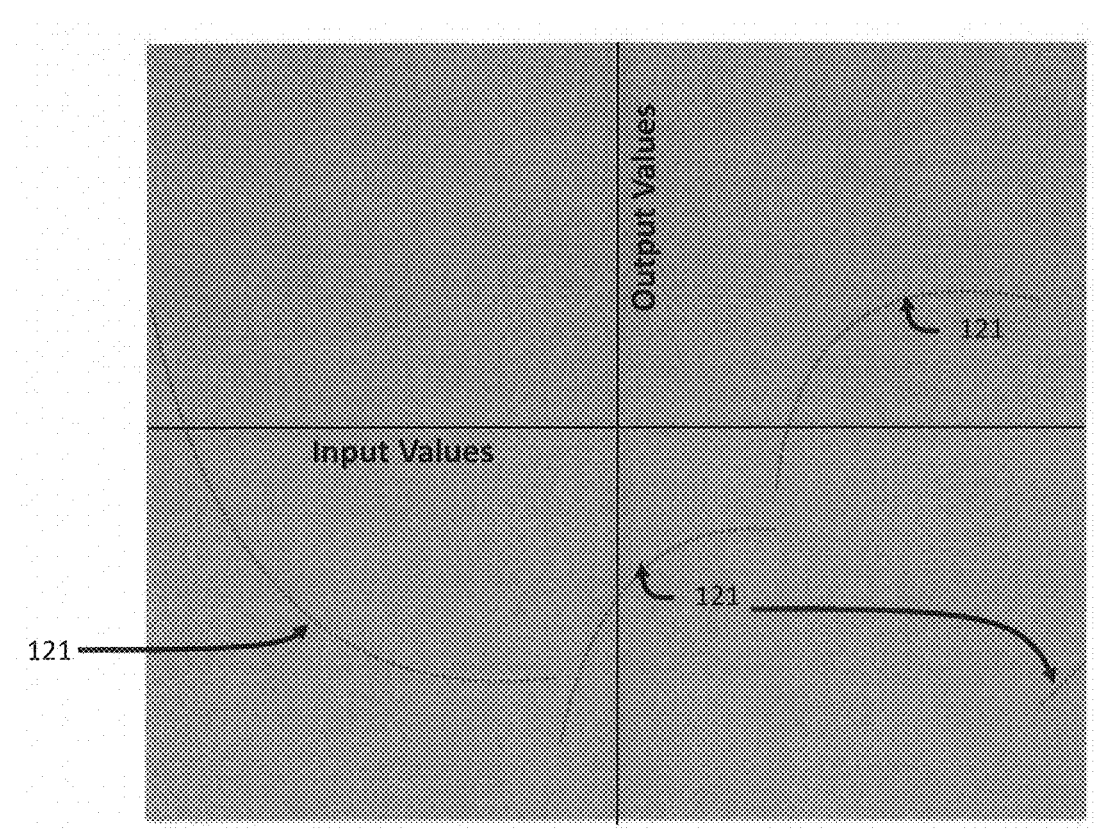
FIG. 1f shows a plot in a coordinate system representative of a non-linear transfer function utilized by at least some embodiments of the invention.

An example of an iterative image process is illustrated in FIG. 1e. Specifically, FIG. 1e illustrates an exemplary fundamental sequencing of the local micro-contrast convergence process whereby an Iterated Function Module 110 approach takes a first image 111 and processes it with a first set of one or more non-linear transfer functions 112 (e.g., local micro-contrast convergence algorithm). The second image created either becomes the final resultant image 120 or, if a next processing step is designed as part of the algorithm, the first iteration image 113 is further processed with a second function 114 (e.g., a second set of one or more non-linear transfer functions) resulting in image 115. The process can be iterated one or more times with different sets of non-linear transfer functions (e.g., a third set of one or more non-linear transfer functions or a fourth set of one or more non-linear transfer functions) applied within a given algorithmic sequence 116 to 119 to output a resultant image 120.

In some embodiments, using a same source image 111, a second Iterated Functional Module can be applied to the same image 111, but applying different functions and number of iterations to reveal different characterizations and relationships among the tissues. Consequently, this Multi-process Sequencing approach can provide two distinct characterizations of the same objects within the same original image.

In some embodiments, two or more of the resultant images can be combined or merged in a Multi-image Synthesis process to create a new resultant image that is a composite of the two resultant images or a composite of one resultant image and the original image. This composite image can be further processed or combined with other resultant images.

Figure if shows a plot in a coordinate system illustrating a discontinuous non-linear transfer function 121 according to at least one embodiment of the invention. Figure if illustrates one example of mapping input values of a input image along the x-axis and output values of an output image along the y-axis. The graphic plot generated from a PLUT illustrates the potential to design discontinuous transformations to apply to images. By using PLUTs with discontinuities in the design of the local micro-contrast convergence algorithms, at least some embodiments of the Iterative Transformation Module process can better differentiate margins of cancers from surrounding tissues, even when the cancers are embedded in dense breast tissue. This is a capability that is very limited with the use of nodal point plotting, or may not be possible at all, when transforming input to output values in images.

Figure 1G:
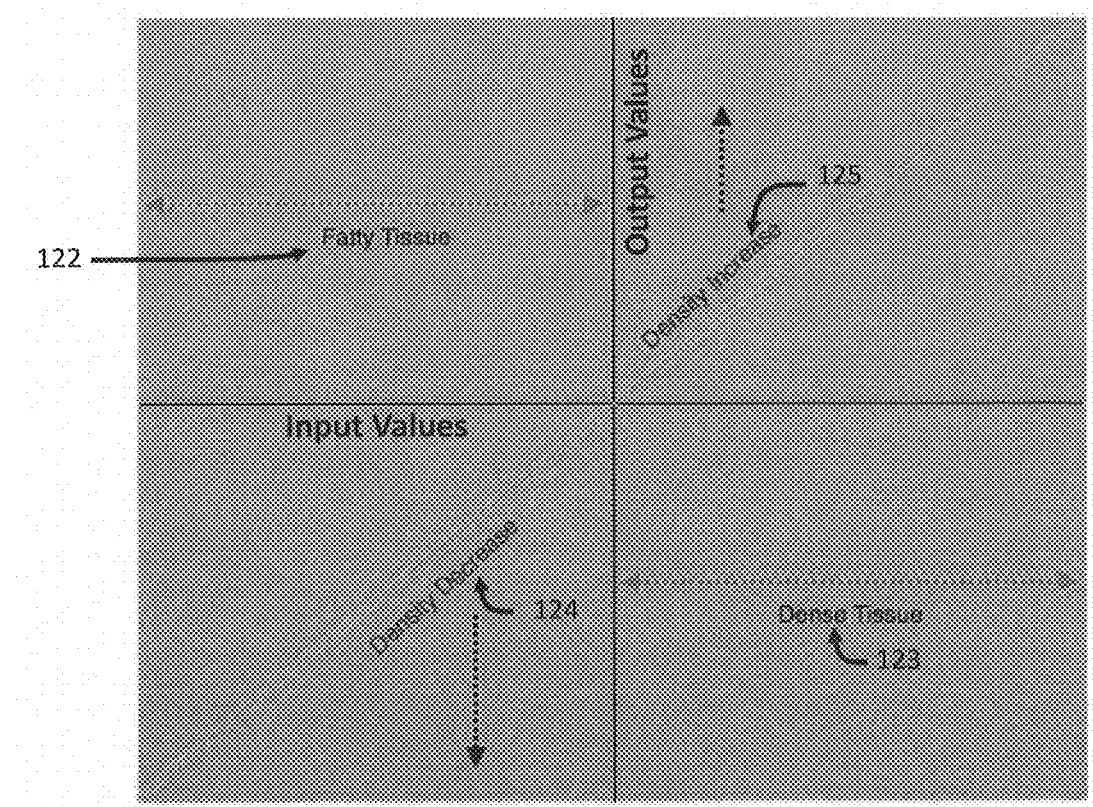
FIG. 1g shows a plot in a coordinate system representative of breast tissue color in a grayscale image utilized by at least some embodiments of the invention.

FIG. 1g shows a plot in a coordinate system illustrating luminance values of breast tissue in a mammogram image. FIG. 1g illustrates one example of mapping input values along the x-axis and output values along the y-axis. Fatty tissue representation 122 is indicated in the luminance area of breast images that contain fatty tissue and dense tissue representation 123 indicates the luminance area of breast images that contain dense tissues. Typically, breast cancer has luminosities much higher than those of fatty tissue. Consequently, it is important to separate fatty tissue from dense tissue. Any remapping of luminosities below the red diagonal line makes that part of an image darker decreasing the density 124, while the those above the line makes the values brighter and increases the density 125. The correlation of this image property distribution with discontinuous nonlinear transformations built into the PLUT design, reduces time needed for developing new algorithms for new diseases and imaging modalities.

Figure 2A:
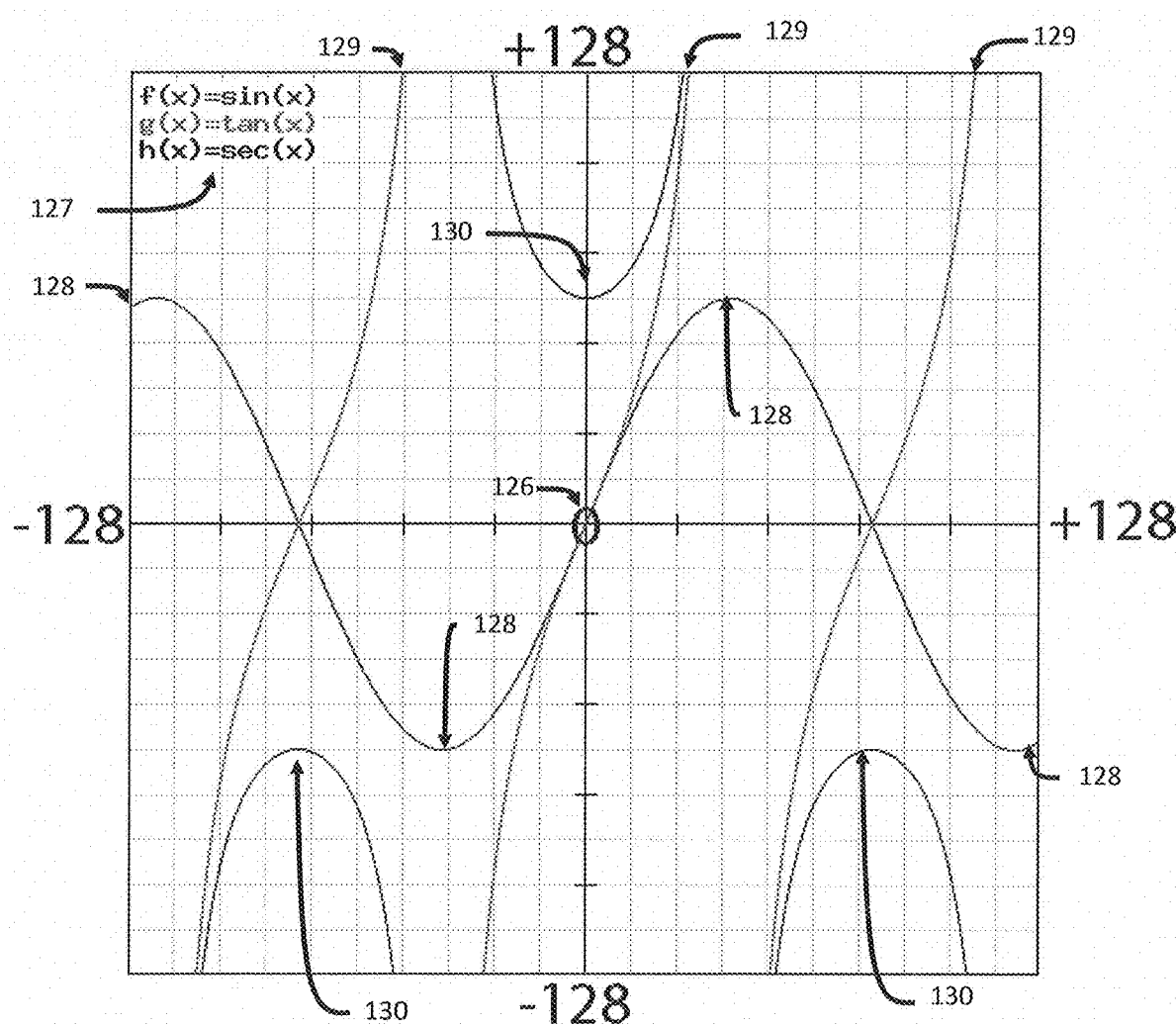
FIG. 2a shows mathematical functions that may be used to generate new profile look up table (PLUT) input and output values according to at least some embodiments of the invention.

FIG. 2a illustrates one embodiment where multiple mathematical functions can be utilized to create possible PLUT values for multiple image channels to create different iterations of a local micro-contrast convergence algorithms for use in applications with new diseases, modalities, and applications beyond medicine. Utilizing computer-based creation of PLUT sequences can greatly speed the process of developing new algorithmic sequences for visualizing new diseases or anomalies.

In FIG. 2a, the x and y axis reflect the input and output values of an image while mid-point 126 specifies one possible position of a mid-point for the coordinate system. FIG. 2a expresses the luminance and color values of an 8-bit image with 256 data points possible for luminance and multiple color channel mapping. Three mathematical functions 127 were plotted automatically and their values indicated within the plot. The blue curve (blue channel) 128 was created using $f(x)=\sin(x)$. The red channel 129 was created using $g(x)=\tan(x)$ and the luminance channel 130 was created using $h(x)=\sec(x)$. The mid-point 126 (or 0 point) can be placed in any position within the coordinate system that best supports the mapping of mathematical functions that can be mapped to a PLUT for optimization of tissue/material visualization and characterization in an automatic, rather than a laborious manual process.

Figure 2B:
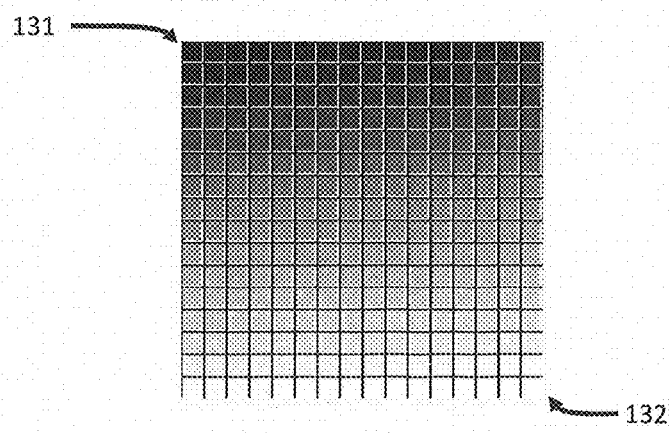
FIG. 2b shows a look-up table (LUT) for an 8-bit grayscale image according to at least some embodiments of the invention.

FIG. 2b shows a matrix representing a grayscale 2D look-up table for an 8-bit grayscale image. Level 0 representing black is in the upper left corner of the grid at 131.

Grayscale luminance levels increase stepwise left to right, and top to bottom until pure white level 255 is reached in the lower right hand corner at 132.

Exemplary Computer System

Figure 2C:
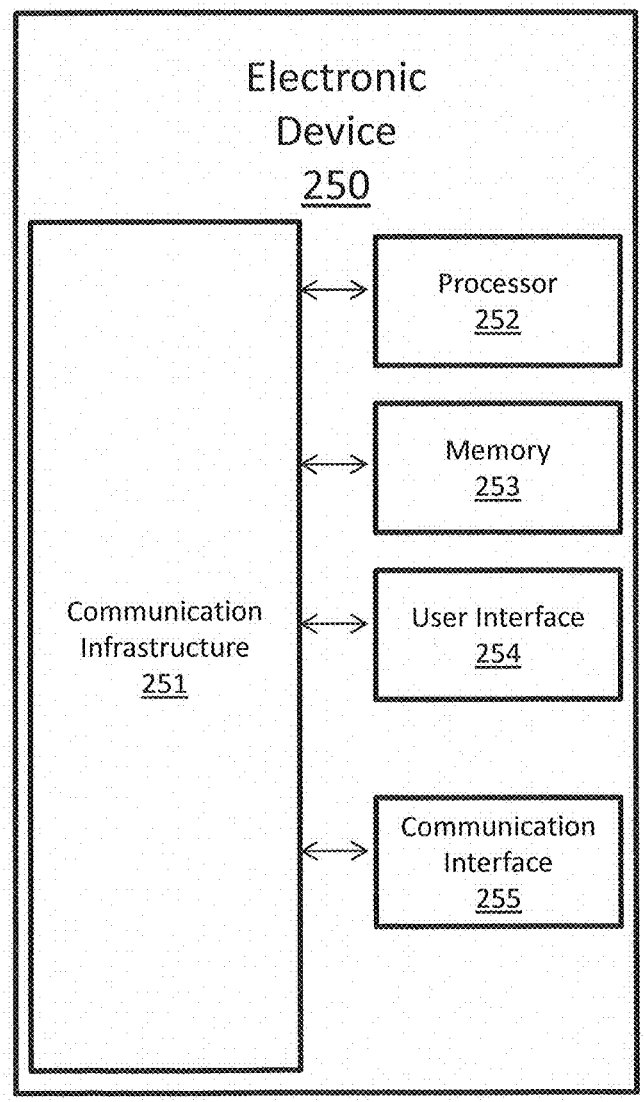
FIG. 2c shows a block diagram that illustrates an electronic device for performing one or more methods according to at least some embodiments of the invention.

FIG. 2c shows a block diagram that illustrates an electronic device 250 for performing one or more methods according to one or more embodiments of the present invention.

Electronic device 250 may be any computing device for receiving data from a user or a remote device, processing data, and generating and/or displaying data. Electronic device 250 may include communication infrastructure 251, processor 252, memory 253, user interface 254 and communication interface 255.

Processor 252 may be any type of processor, including but not limited to a special purpose or a general-purpose digital signal processor. In this embodiment, processor 252 is connected to a communication infrastructure 251 (for example, a bus or network). Various software implementations are described in terms of this exemplary computer system.

Memory 253 may include at least one of: random access memory (RAM), a hard disk drive and a removable storage drive, such as a floppy disk drive, a magnetic tape drive, or an optical disk drive, etc. The removable storage drive reads from and/or writes to a removable storage unit. The removable storage unit can be a floppy disk, a magnetic tape, an optical disk, etc., which is read by and written to a removable storage drive. Memory 253 may include a computer usable storage medium having stored therein computer software programs and/or data to perform any of the computing functions of electronic device 250. Computer software programs (also called computer control logic), when executed, enable electronic device 250 to implement embodiments of the present invention as discussed herein. Accordingly, such computer software programs represent controllers of electronic device 250. Memory 253 may include one or more data stores that store imaging data, software files or any other types of data files.

User interface 254 may be a program that controls a display (not shown) of electronic device 250. User interface 254 may include one or more peripheral user interface components, such as a keyboard or a mouse. The user may use the peripheral user interface components to interact with electronic device 250. User interface 254 may receive user inputs, such as mouse inputs or keyboard inputs from the mouse or keyboard user interface components. User interface 254 may display imaging data on the display of electronic device 250.

Communication interface 255 allows imaging data to be transferred between electronic device 250 and remote devices. Examples of communication interface 255 may include a modem, a network interface (such as an Ethernet card), a communication port, a Personal Computer Memory Card International Association (PCMCIA) slot and card, etc. Imaging data transferred via communication interface 251 are in the form of signals, which may be electronic, electromagnetic, optical, or other signals capable of being transmitted or received by communication interface. These signals are provided to or received from communication interface 251.

Exemplary Local Micro-Contrast Algorithms

Figure 3A:
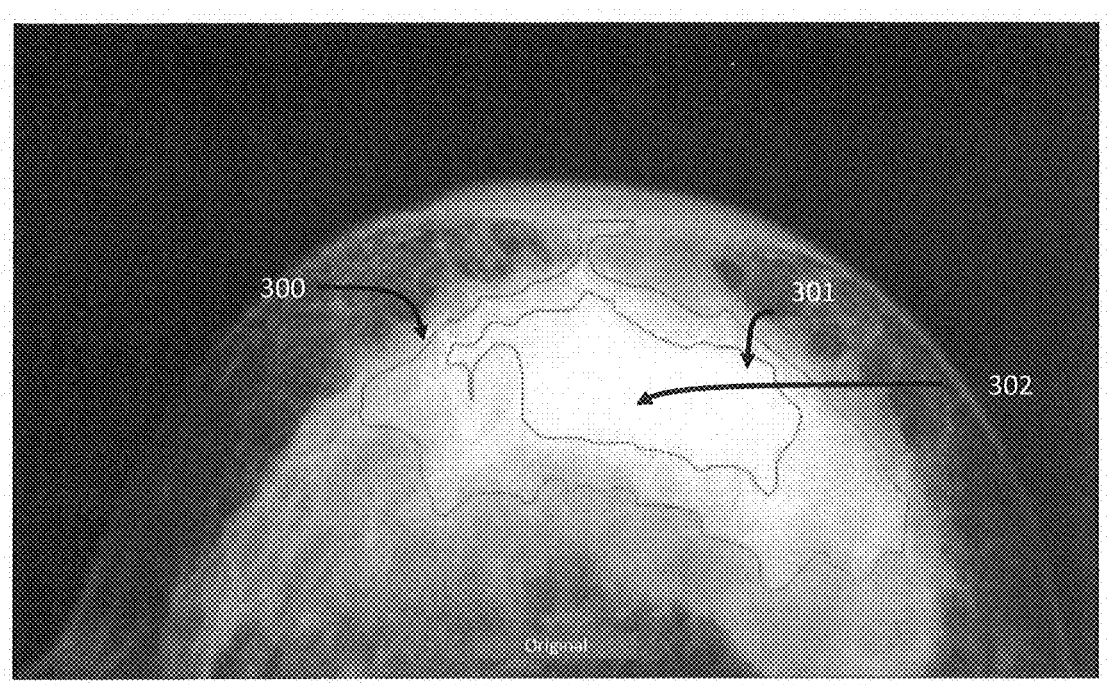
FIG. 3a shows an exemplary high density original X-ray mammogram containing cancer in the brightest area of the image.

FIG. 3a shows a mammogram containing very dense breast with high density outlined at 300. The outline at 301 defines the boundary of extreme density containing cancer at 302.

Figure 3B:
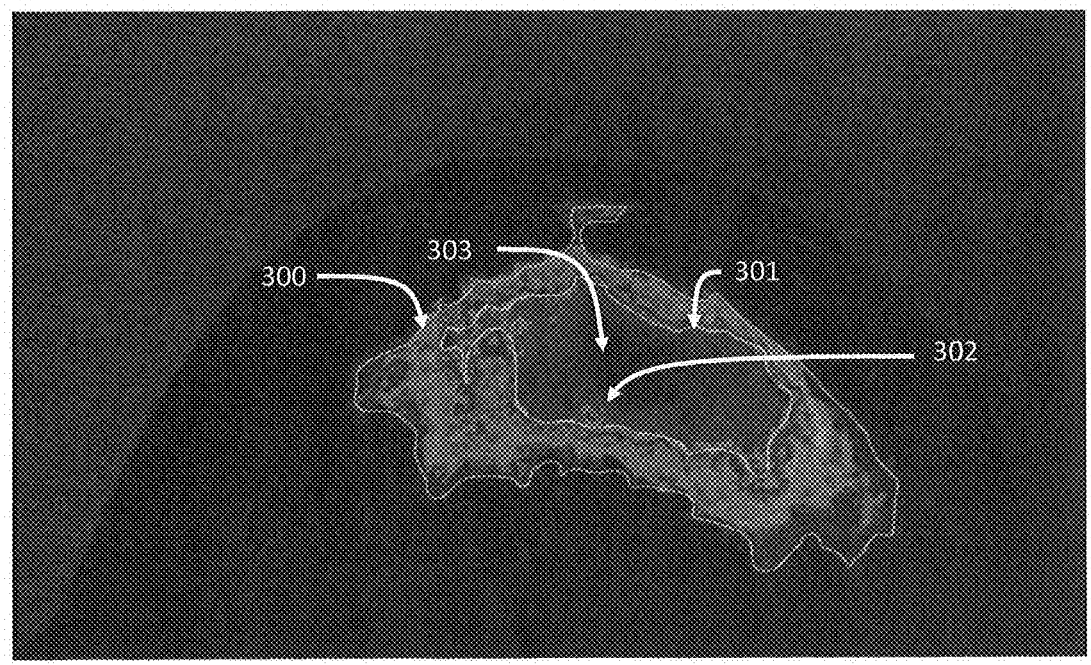
FIG. 3b shows an exemplary mammogram image after applying local micro-contrast convergence algorithm sequence to create the resultant image using one or more methods according to at least some embodiments of the invention.

FIG. 3b shows an exemplary mammogram image after processing the image using one or more methods described herein. In this embodiment, only the highest density areas of the breast are revealed in color. Fatty and other low-density areas of the breast image are indicated in black at 303. Density increases are indicated in steps proceeding from the outer boundary in green 300 and progressing inward to the blue 302 and finally black area in the center 303 where the greatest development of the cancer exists. Each color represents a quantifiably different level of breast density. This quantification provides precise reporting for the American College of Radiology BI-RADS specification to indicate the presence of dense breasts in a woman's mammograms. Additionally, however, this process can extend the BI-RADS reporting system to go beyond a simple overall percentage of the breast density. It can quantify multiple levels of breast density, specify their distribution, and estimate possible risk for the woman. These methods are adaptive and compensate for the extreme variability in mammographic image presentations influenced by differences in the size of the breast, the density of the breast, changes during pregnancy, changes with aging and menopause, alterations based on the development of cysts, fibro adenomas, calcifications, the presence of lesions, and scarring due to trauma, surgeries, and biopsies.

Computational Intelligence (CI) Algorithm

Embodiments of the CI algorithm is designed to optimize the expression of high-density abnormalities in breast tissues by processing original grayscale mammograms and revealing the abnormality's boundaries and internal structures. The algorithmic sequence provides significant color and brightness differentiation between the abnormalities and other normal tissues such that it is easier for clinicians and patients to readily observe areas of concern.

Figure 4K:
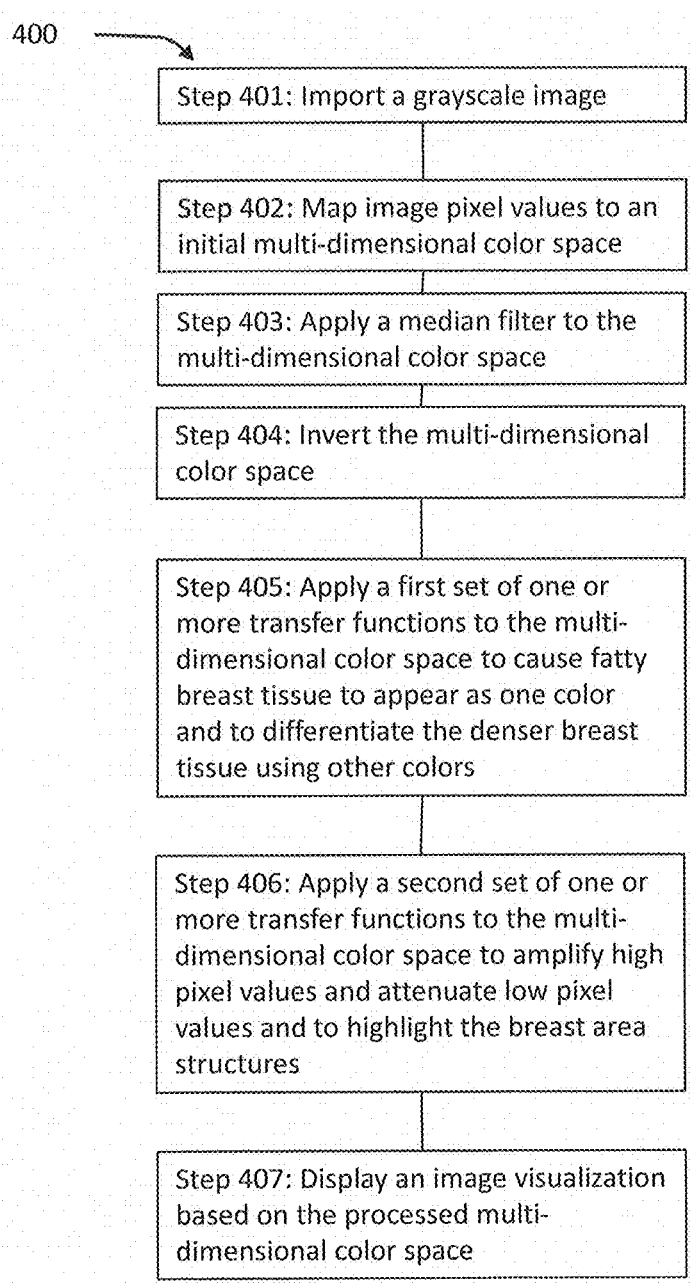

FIG. 4k is a flow chart illustrating a method 400 for creating a visualization from a grayscale image, according to at least one embodiment of the invention.

At step 401, processor 252 imports a grayscale image. FIG. 4a shows an exemplary grayscale image of a mammogram, according to at least one embodiment of the invention. FIG. 4d shows a horizontal gradient representation of FIG. 4a. The gradient grayscale image provides the full range of luminance levels, as compared with the range different mammograms have, so that the full range of colors expressed in the local micro-contrast convergence algorithmic sequence can be illustrated. Each step of the algorithmic sequence described in FIG. 4k can applied to both the mammograms and the gradients, again, for illustration and comparative purposes.

In some embodiments, a processor 252 receives or imports an image (e.g., grayscale).

In some embodiments, the image is imported from memory 253. In other embodiments, the image is imported from a remote device via communication interface 251.

In some embodiments, the grayscale image is imported for processing as an input array or matrix with x and y pixel dimensions and z bits of grayscale or color depth. In some embodiments, the matrix may contain values of 8, 10, 12, 14 or 16 bits of luminance per pixel (Lp). (Lp) is the luminance value of each pixel (p) at a position (x, y) in the original image. As the number of bits increase, the greater number of variations in a pixel value also increases. For example, if 8 bits are used, then $2^8$ possible pixel values may be assigned to each pixel. On the other hand, if 16 bits are used, then $2^{16}$ possible pixel values may be assigned to each pixel. By increasing the number of possible pixel values, the image processing methods described herein can increase the variations in the final image.

At step 402, processor 252 maps the grayscale image to a multi-dimensional color space.

In some embodiments, to map the grayscale image, the grayscale image is replicated into additional matrices of identical x/y coordinates for each color component and luminance value to form an n-dimensional super-positioned matrix space of color space layers, where n>1 forms a new matrix set containing voxels.

In some embodiments, the grayscale image is replicated using the following equation:

$$f(Lp)=Cp,$$

where the pixel values at each x/y coordinate in the original is mapped to corresponding x/y coordinate in each color space layer of the multi-dimensional color space of C.

In one embodiment where n=4, an RGB multi-dimensional color space can be defined in terms of four different components: luminance, red, green, and blue. In these embodiments, the RGB multi-dimensional color space includes a luminance color space layer, and first, second and third color space layers corresponding to blue, red and green, respectively. The new matrix C will contain pixel values where R=G=B=Luminance for each pixel value and these pixel values are equal to the grayscale image luminance values (Lp). In some embodiments, there can be a separate luminance only channel or, in other embodiments, the luminance can be generated as a composite of the three other channels. In another embodiment, the values can also be expressed for other values of n where, for example, n has 3 values luminance, saturation, and hue.

One of ordinary skill in the art will appreciate that these embodiments are operable on matrices of n-dimensions that can be visualized in a wide range of color image formats other than the color image formats described herein. The processing of each mammogram (or other image) begins with a multi-channel matrix or image. Additional color spaces may also occur in color spaces such as HSV, CMYK, CIEXYZ or CIELAB using either xyz or cylindrical color spaces.

At step 403, processor 252 applies a median filter to the multi-dimensional color space. In some embodiments, a median filter may refer to a nonlinear digital image processing technique, which preserves edges of objects in the multi-dimensional color space while removing noise. Noise reduction can improve the results of later processing.

In some embodiments, the median filter is applied to each pixel in the multi-dimensional color space by replacing each pixel value with the median of neighboring pixel values. The pattern of neighbors may be referred to as the "window", which slides, pixel by pixel, over the entire image. In some embodiments, the median filter is a 3×3 or radius=1 median filter. In other embodiments, a radius greater than 1 and matrix combinations such as 5×5, 7×7 can be used.

At step 404, processor 252 inverts the image whereby black (0) becomes white (255) and white becomes black. All other values are proportionally inverted except the midpoint of the image values.

At step 405, processor 252 applies a first set of one or more (e.g., PLUT) non-linear transfer functions to the multi-dimensional color space (e.g., RGB). Representation of the resultant images are shown in FIGS. 4b and 4e.

FIG. 4g shows the color values of the CI PLUT 1 (2D look-up tables) that have been optimized to reveal breast structures in this local micro-contrast convergence algorithmic sequence after being applied to the image in FIG. 4a.

FIG. 4i shows a Cartesian plot illustrating a representation of an exemplary (e.g., PLUT) transfer function applied by the processor 252 to the multi-dimensional color space to attenuate low-density breast tissue according to at least one embodiment of the invention. In this Cartesian plot, the color space layer input is shown on the x-axis, with values ranging from −128 to +128. The corresponding output after the (e.g., PLUT) transfer function is shown on the y-axis, where the midpoint of the luminance levels of an image are at 0 and the values range from −128 to +128. It can be observed that the 0 position in the coordinate plot may be placed at any position in the x/y coordinate space.

In FIG. 4i, the red channel is shown at 408, the green channel is 409, and the luminance channel is 410. In some embodiments, a first (e.g., PLUT) transfer function (as shown in FIG. 4i) is applied to the luminance color space layer to attenuate low-density fatty breast tissue. In some embodiments, the low density fatty breast tissue has a luminance value in the lower 50% range; the lower 40% range; the lower 30% range; the lower 20% range; or the lower 10% range.

At this stage in processing, areas that do not hold a possibility of having cancer have been separated from those where possible cancer or other abnormalities can occur. Additionally, any lesions in the image now begin to form boundaries and express internal morphological structures as micro-contrast neighborhoods converge. Compared with the diffuse grayscale mammographic image, visually distinguishable boundaries have been formed based on tissue structures. An issue associated with a phenomenon known as center-surround effect, and limits human visual perception has been minimized or eliminated. Gray values are differentially interpreted by the human vision system based on what is around the object. The same object may look brighter against a dark background and darker against a light background. At least some embodiments of the invention may allow PLUT values to be determined that eliminate the center surround issue affecting perception and detection of cancer in mammograms; based on optimal settings for human vision differentiation based on color perception theory, the image that the clinician is seeing after the transformation provides greatly enhanced diagnosis potential for the tissues being examined.

Turning back to FIG. 4k, at step 406, processor 252 applies a second set of one or more transfer functions to the multi-dimensional color space.

FIG. 4h shows the color values of the CI PLUT 2 (2D look-up table) that has been optimized to reveal breast structures in this local micro-contrast convergence algorithmic sequence after being applied to the image in FIG. 4b.

FIG. 4i shows a Cartesian plot illustrating a representation of an exemplary (e.g., PLUT) set of transfer functions applied by the processor 252 to the multi-dimensional color space. In FIG. 4i, the red channel is indicated at 411 and luminance channel at 412 are graphic representations of CI PLUT 2 lookup table in FIG. 4h.

In this Cartesian plot FIG. 4i, the color space layer input is shown on the x-axis, with values ranging from −128 to +128. The corresponding output after the transfer function (shown visually in FIG. 4i) is shown on the y-axis, where the midpoint of the luminance levels of an image are at 0 and the values range from −128 to +128. In these embodiments, the values are applied to the resultant image in FIG. 4b to cause fatty breast tissue to appear as one color in FIG. 4c (e.g., blue and magenta) and to differentiate the denser breast tissue (gold and red), and breast boundary (green) using other colors.

FIGS. 4c and 4f show exemplary image representations of a mammogram and gradient image based on the multi-dimensional color space after applying an exemplary second set of one or more non-linear transfer functions to cause low density breast tissue to appear as one color and differentiate high density breast tissue, according to at least one embodiment of the invention. In FIG. 4c, the cancer is revealed in gold 413 and surrounded by black.

The values of the high-density areas of a breast image measured in RGB values in FIG. 4c at 413 are Red>250/ Green>165/Blue<50.

In some embodiments, the design concept of these transfer functions are employed to attenuate pixel values in areas of a mammogram outside of the breast tissue. As a result, one component of the transfer function values in the PLUT reduce eyestrain on clinicians in the final image by assigning a value to the areas of the mammogram outside of the breast so as not to interfere with patterns inside the breast area.

At step 407, processor 252 displays a visualization image (e.g., FIG. 4c) based on the processed multi-dimensional color space.

Each step of this process further transforms a grayscale mammogram (and it also works for Mill and ultrasound images of the breast) into color patterns that clearly defined boundaries of abnormal tissues as well as reveal structures of normal breast tissue, regardless of size. In this image visualization, cancerous lesions have distinctive patterns that separate themselves from all other abnormal and normal tissue structures.

In the CI visualizations, differences in the characterization of both cancer and benign lesions in the visualizations can be differentiated using histogram analysis. The boundaries of cancer are clearly defined in the CI visualizations. In addition, differences in structure inside the boundaries of the cancer are indicated with characteristic colors and shapes. This makes it easier for radiologists to identify boundaries of cancerous and benign structures. For example, in the CI visualizations, the greater the number of color changes within the boundaries of the cancer, the more advanced the development of the cancerous tissue. Changes in tissue surrounding cancerous and benign lesions are also revealed in the CI visualizations. It is possible that the CI visualizations may also reveal angiogenesis occurring at the boundaries of cancerous lesions.

In addition to the differentiations described above, in the CI visualizations, radial scars vs. cancerous lesions and cancerous lesions vs. fibro adenomas are differentiated. The CI visualizations also indicate the presence of developing cancer within milk ducts before it has become invasive and surrounding breast tissue. Cancerous tissues can be correlated with the presence of microcalcifications.

Cancerous lesions, as well as all other structures, can be correlated between different views of mammograms for a woman such as Cranial-Caudal (CC or view from above) and Mediolateral-oblique (MLO or angled view) and be used to correlate data between studies at different times. The internal structure characterized for cancer by these methods is so precise that it can be used to guide surgeons performing biopsies, lumpectomies, and for determining progress for a patient undergoing treatment for cancer.

LD Algorithm

Embodiments of the invention regarding the LD algorithm provide visualizations that are designed to emphasize extremely fine structures and details in an image (e.g.,  original mammogram) that occur in the very low density areas of the image. Diagnostically important structures such as spiculations and low attenuating lesions become clearly defined.

Figure 5A:
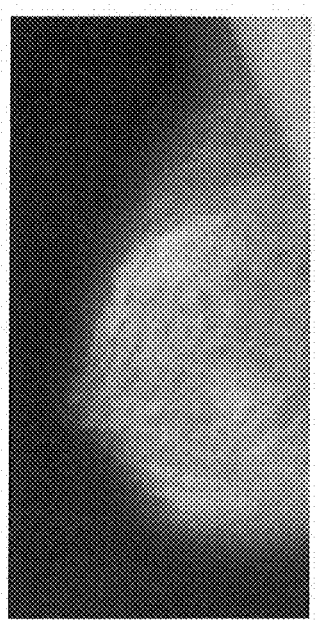
FIGS. 5a to 5i show an exemplary local micro-contrast convergence algorithmic sequence to process mammographic images to reveal low attenuating breast tissues in resultant grayscale images according to at least some embodiments of the invention.
Figure 5B:
Figure 5C:
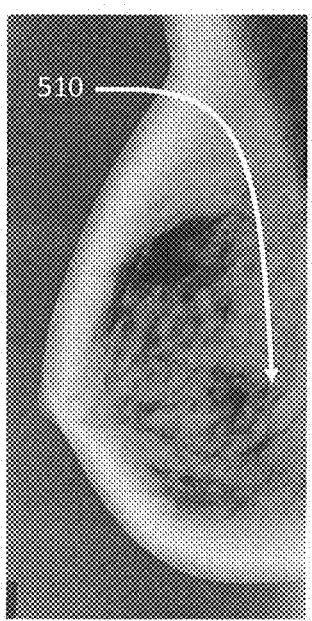
Figure 5D:
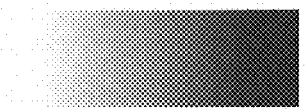
Figure 5E:
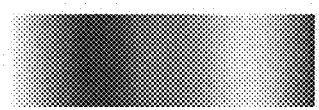
Figure 5F:
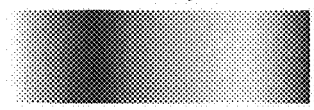
Figure 5G:
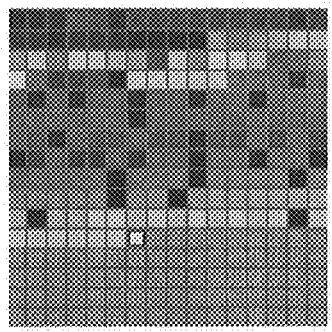
Figure 5H:
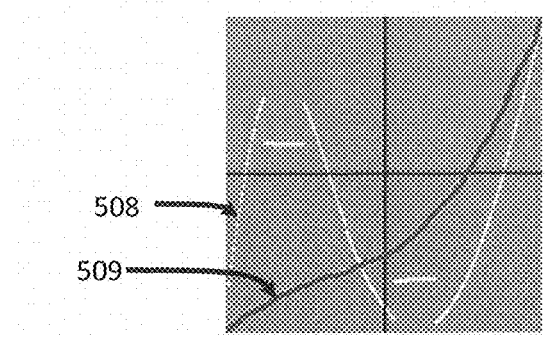
Figure 5I:
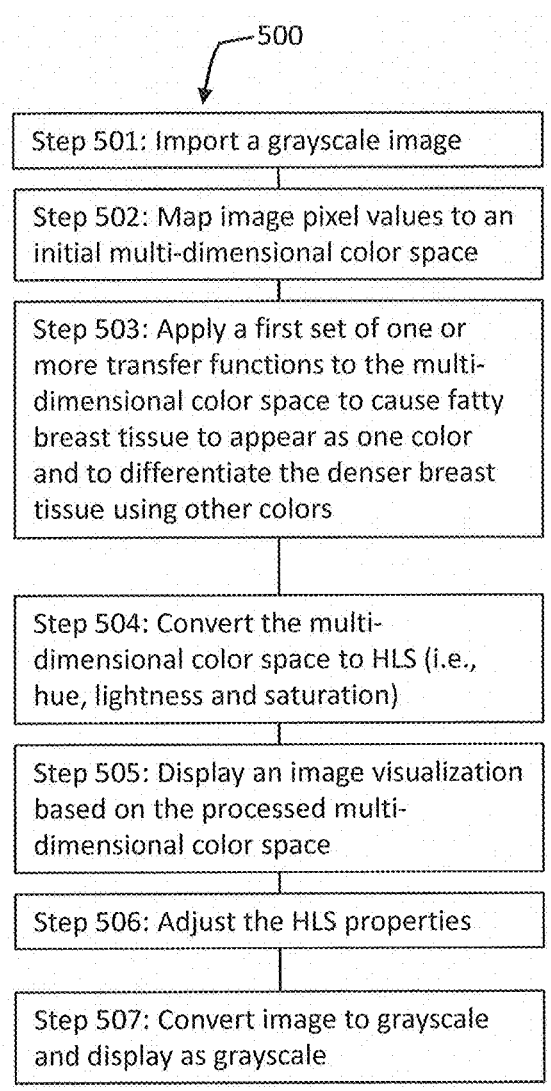

FIG. 5i is a flow chart illustrating a method 500 for creating a LD visualization from a grayscale image, according to at least one embodiment of the invention.

At step 501, processor 252 imports a grayscale image. FIG. 5a shows an exemplary grayscale image of a mammogram, according to at least one embodiment of the invention. FIG. 5d shows a horizontal gradient representation of 256 grayscale values from black to white.

At step 502, processor 252 maps the grayscale image to a multi-dimensional color space. The grayscale mapping at step 502 is substantially similar to the grayscale mapping in step 402 above.

At step 503, processor 252 applies a first set of one or more transfer functions (e.g., a local micro-contrast convergence algorithm PLUT) to the multi-dimensional color space. Examples of the one or more transfer functions are illustrated in FIGS. 5g and 5h.

FIG. 5h shows a Cartesian plot illustrating a representation of an exemplary (e.g., PLUT) transfer function applied by the processor 252 according to at least one embodiment of the invention. In some embodiments, a first transfer functions is applied to the luminance color space layer 508 to brighten low-density areas of the breast image while attenuate high-density breast areas. A second transfer function representing a red channel 509, colorizes the breast parenchyma while leaving the dense tissue dark. In some embodiments, the low density fatty breast tissue has a luminance value in the lower 50% range; the lower 40% range; the lower 30% range; the lower 20% range; or the lower 10% range. The design of this local micro-contrast convergence algorithm, and its related PLUT values, function to reveal details in any portion of the image regardless of the percentage of low density in the breast.

Representation of the resultant images produced after step 503 are shown in FIGS. 5b and 5e.

At step 504, the multi-dimensional color space (represented as color image shown in FIG. 5b) is now converted to an HSL color space. In this embodiment, RGB values are converted to luminance, hue, and saturation values, as shown below in the following example:

(Hue, Saturation, Lightness, Zone)
(0.0, 0.0, 0.2, Red)
(0.0, 0.0, 0.1, Cyan)
(0.0, −1.0, 0, Master)

The image can be displayed first in RGB color or after conversion in HSL color space in step 505.

The image in FIG. 5c (and corresponding image 5f) is created from the image in FIGS. 5b and 5e by setting the master saturation for all hues in the HSL color space to −100% saturation. As a result, hue is no longer a factor in the expression of the image. Luminance values however, are still adjustable and changing the luminance values of various hues in the color space can alter the grayscale representation of those values. In some embodiments, the red and cyan luminance values are adjusted to 0.2 and 0.1 respectively. This brightens the gray values of the general breast background, highlights the interior portion of dense tissues such as cancerous lesions, and creates separation between the fine structure and the fatty tissue of the breast. The image can be converted to a single channel image containing only luminance in step 507 (and shown in FIG. 5c).

At this stage in processing, areas very fine structures associated with low-density luminance values are separated from the low-density, low-frequency areas 510 of the breast parenchyma, boundary, and chest wall. Compared with the diffuse grayscale mammographic image, visually distinguishable boundaries have been formed based on tissue structures.

HD Algorithm

Embodiments of the invention regarding the HD algorithm provide visualizations that are designed to reveal details in an image (e.g., original mammogram) that occur in the very highest density areas of the image. Structures such as breast abnormalities and cancerous lesion are revealed from the surrounding dense bright/white areas and become clearly defined.

Figure 6A:
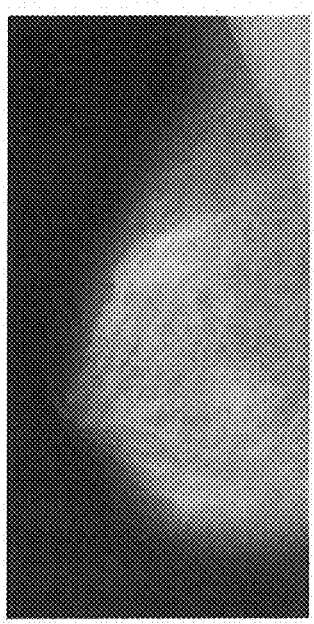
Figure 6D:
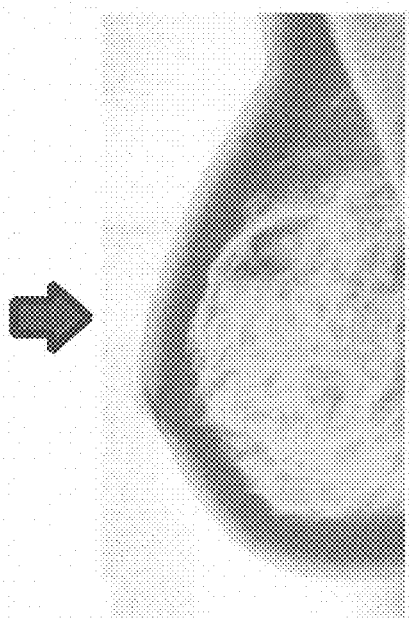
Figure 6D:
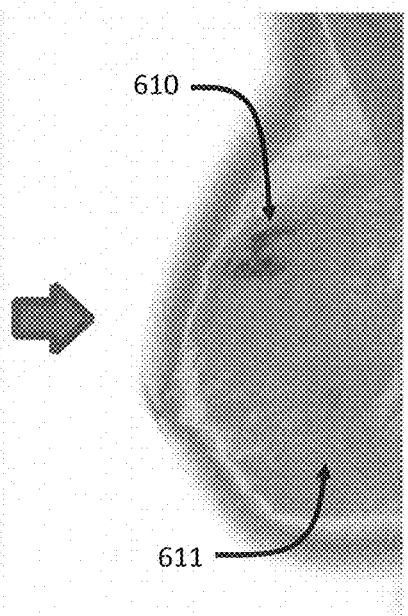
Figure 6D:
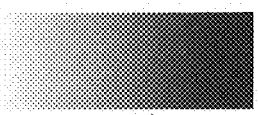
Figure 6E:
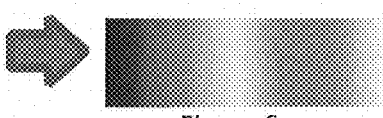
Figure 6F:
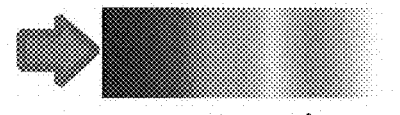
Figure 6G:
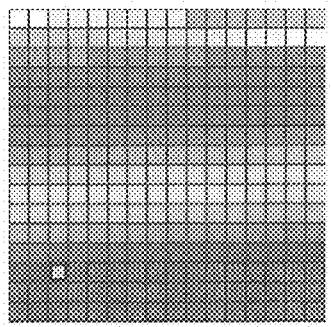
Figure 6H:
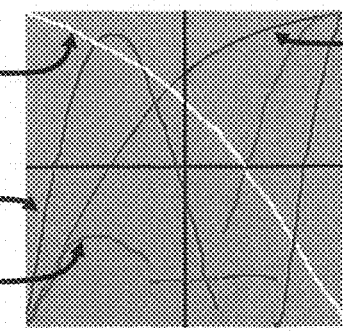
Figure 6I:
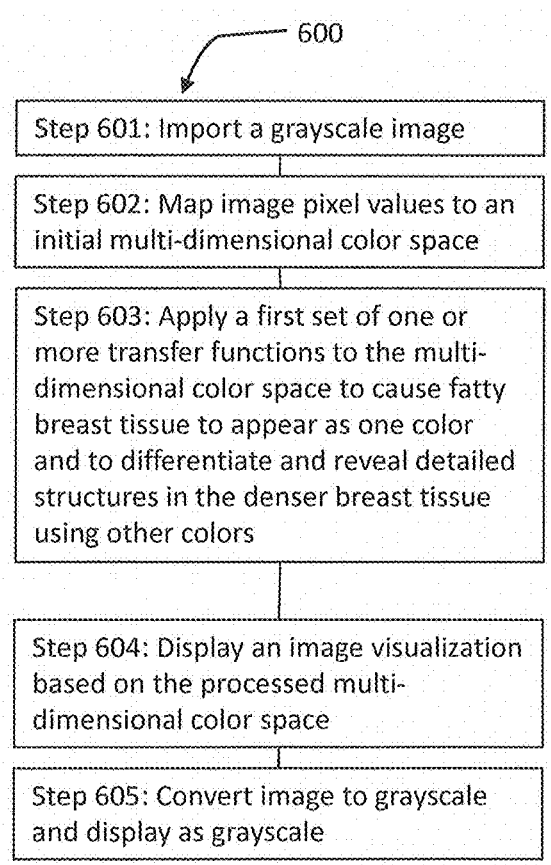

FIG. 6i is a flow chart illustrating a method 600 for creating a HD visualization from a grayscale image, according to at least one embodiment of the invention.

At step 601, processor 252 imports a grayscale image. FIG. 6a shows an exemplary grayscale image of a mammogram, according to at least one embodiment of the invention.

At step 602, processor 252 maps the grayscale image to a multi-dimensional color space.

At step 603, processor 252 applies a first set of one or more non-linear transfer functions (e.g., HD PLUT 1 local micro-contrast algorithm) to the multi-dimensional color space. Representations of the first set of one or more non-linear transfer functions are shown in FIGS. 6g and 6h respectively. FIG. 6g shows the color values of the LD PLUT (look-up table) that has been optimized to reveal breast structures in mammographic images. FIG. 6h show graphic representations in a coordinate system (e.g., that can be created from the PLUTs in FIG. 6h). In these embodiments, a first transfer function is applied to the luminance color space layer to invert the luminance values 606 of the breast image. A red channel 607 amplifies the low-density areas of the image while attenuating high-density breast areas. The green channel 608, graphically shown in FIG. 6h as a discontinuous mapping of green channel values, colorizes the breast boundary and contributes with the red channel to make the breast background a yellow color. In some embodiments, the high-density breast tissue is greater than a lower 50% range; a lower 40% range; a lower 30% range; a lower 20% range; or a lower 10% range. The blue channel 609 adds color to define the outer boundary of the breast. The design of this local micro-contrast convergence algorithm, and its related PLUT values, can function to reveal details in any portion of the image regardless of the percentage of high density in the breast.

At this stage in processing, areas of the image containing very high density structures 610 are separated from the low-density areas 611 of the breast parenchyma, boundary, and chest wall and cancer is further distinguished from among other high-density areas of the breast. Compared with the diffuse grayscale mammographic image, visually distinguishable boundaries have been formed based on tissue structures.

The image can then be displayed in multi-dimensional color space step 604 (e.g., as shown in FIG. 6b) or converted to a grayscale image at step 605 before being displayed (e.g., FIG. 6c) using a weighted conversion of R, G, and B values to achieve a luminance value according to the following formula: 0.30*R+0.59*G+0.11*B=luminance value.

MC Algorithm

Embodiments of the invention regarding the MC algorithm provide visualizations that are designed to reveal details in an image (e.g., original mammogram) that occur in the very highest density areas of the image, mainly small structures such as calcifications are revealed from the surrounding dense bright/white areas and become clearly defined.

Figure 7A:
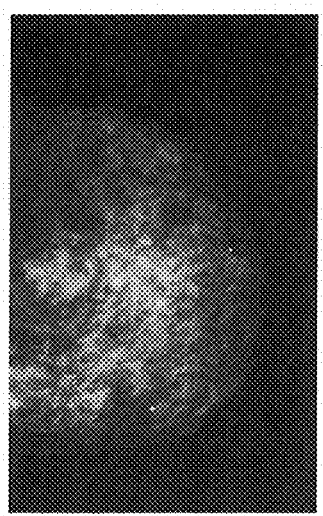
Figure 7B:
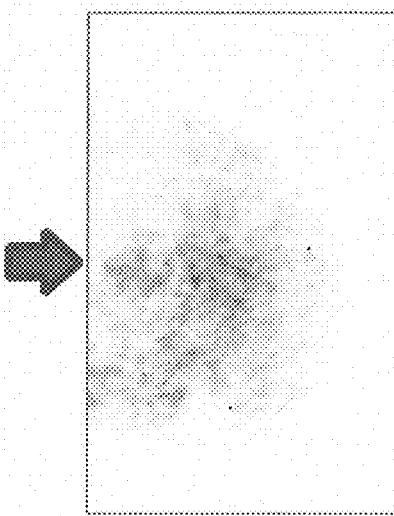
Figure 7C:
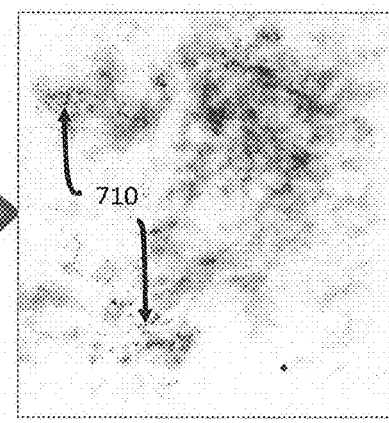
Figure 7D:
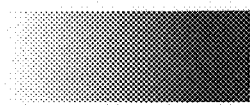
Figure 7E:
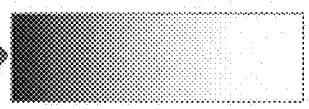
Figure 7H:
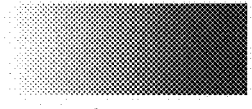
Figure 7H:
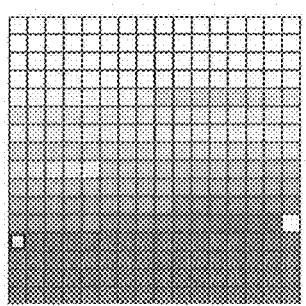
Figure 7I:
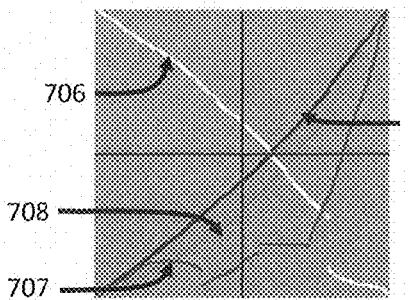
Figure 7J:
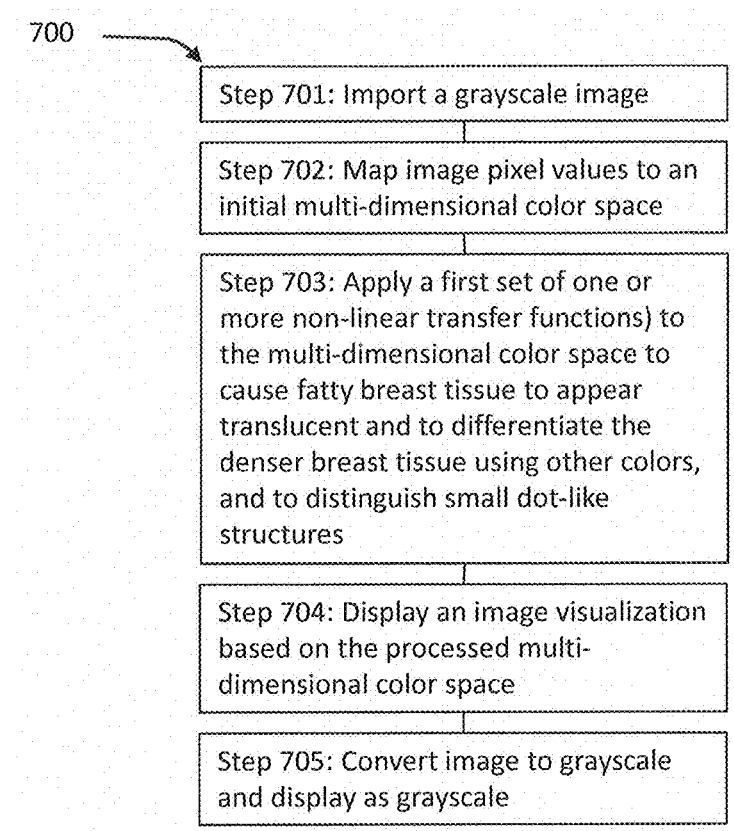

FIG. 7j is a flow chart illustrating a method 700 for creating a MC visualization from a grayscale image, according to at least one embodiment of the invention.

At step 701, processor 252 imports a grayscale image. FIG. 7a shows an exemplary grayscale image of a mammogram, according to at least one embodiment of the invention.

At step 702, processor 252 maps the grayscale image to a multi-dimensional color space.

At step 703, processor 252 applies a first set of one or more transfer functions (e.g., MC PLUT 1 local micro-contrast convergence algorithm) to the multi-dimensional color space. Representations of the local micro-contrast convergence algorithm are shown in FIGS. 7h and 7i. FIG. 7h shows the color values of the MC PLUT (look-up table) that has been optimized to reveal breast structures in mammographic images. FIG. 7i show graphic representations in a coordinate system. In these embodiments, a transfer function is applied to the luminance space 706, to discontinuously invert the luminance values of the breast image. The red channel 707 attenuates a large portion of the image employing a discontinuous mapping of red channel values. The green channel 708 values contribute to creating a brown tone to the high-density areas of the breast. The blue channel 709 slightly tints the fatty tissue area of the breast.

The design of this local micro-contrast convergence algorithm, and its related PLUT values, function to reveal the presence of micro-calcifications in any portion of the image regardless of the percentage of high density in the breast.

At this stage in processing, micro-calcification structures, even in very high density areas of the image, are separated from among other high-density areas of the breast. Compared with the diffuse grayscale mammographic image, visually distinguishable calcifications have been more clearly revealed.

The image can then be displayed in multi-dimensional color space at step 704 (e.g., FIG. 7b) or converted to a grayscale image at step 705 (e.g., FIG. 7c) using a weighted conversion of R, G, and B values to achieve a luminance value according to the following formula: 0.30*R+0.59*G+0.11*B=luminance value. FIG. 7c is an enlarged section of the image in FIG. 7b after being converted to grayscale. The small black microcalcifications 710 can be distinguished from the light background more easily than in the original image.

RF Algorithm

Embodiments of the invention regarding the RF algorithm provide visualizations that are designed to emphasize extremely fine structures and details in an image (e.g., original mammogram). Structures such as spiculations and milk ducts are clearly defined as are structures within high density areas of the rest including those of cancer. In some embodiments, the relief visualization is shown as an overlay on the original image to improve visibility by a user (e.g., radiologist).

Figure 8T:
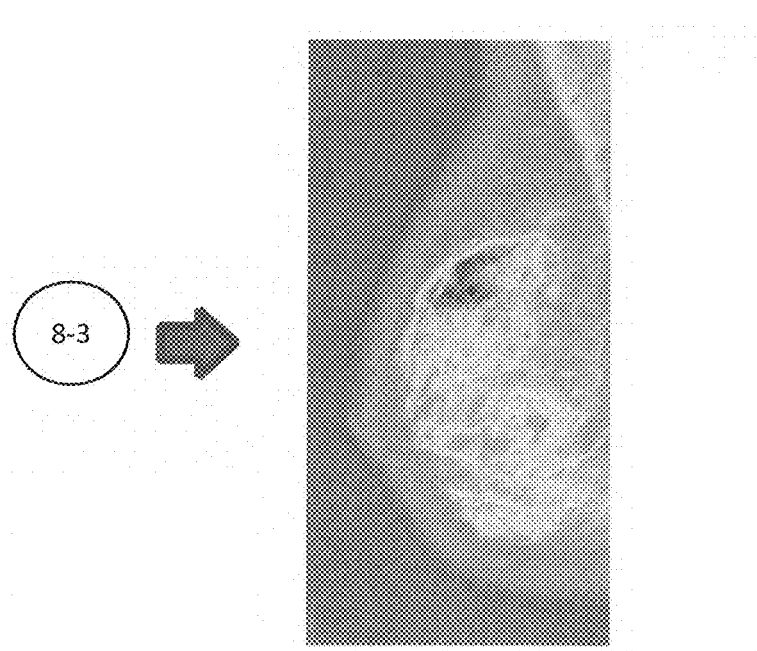
FIGS. 8a to 8u show an exemplary local micro-contrast convergence algorithmic sequence to process mammographic images to reveal details of very fine breast tissue structures in resultant grayscale images according to at least some embodiments of the invention.
Figure 8T:
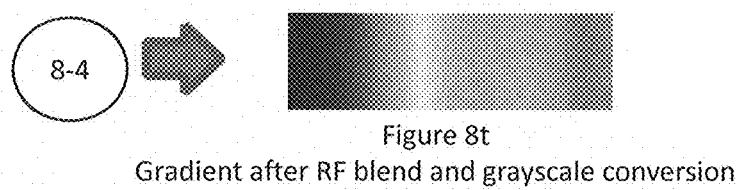
Figure 8U:
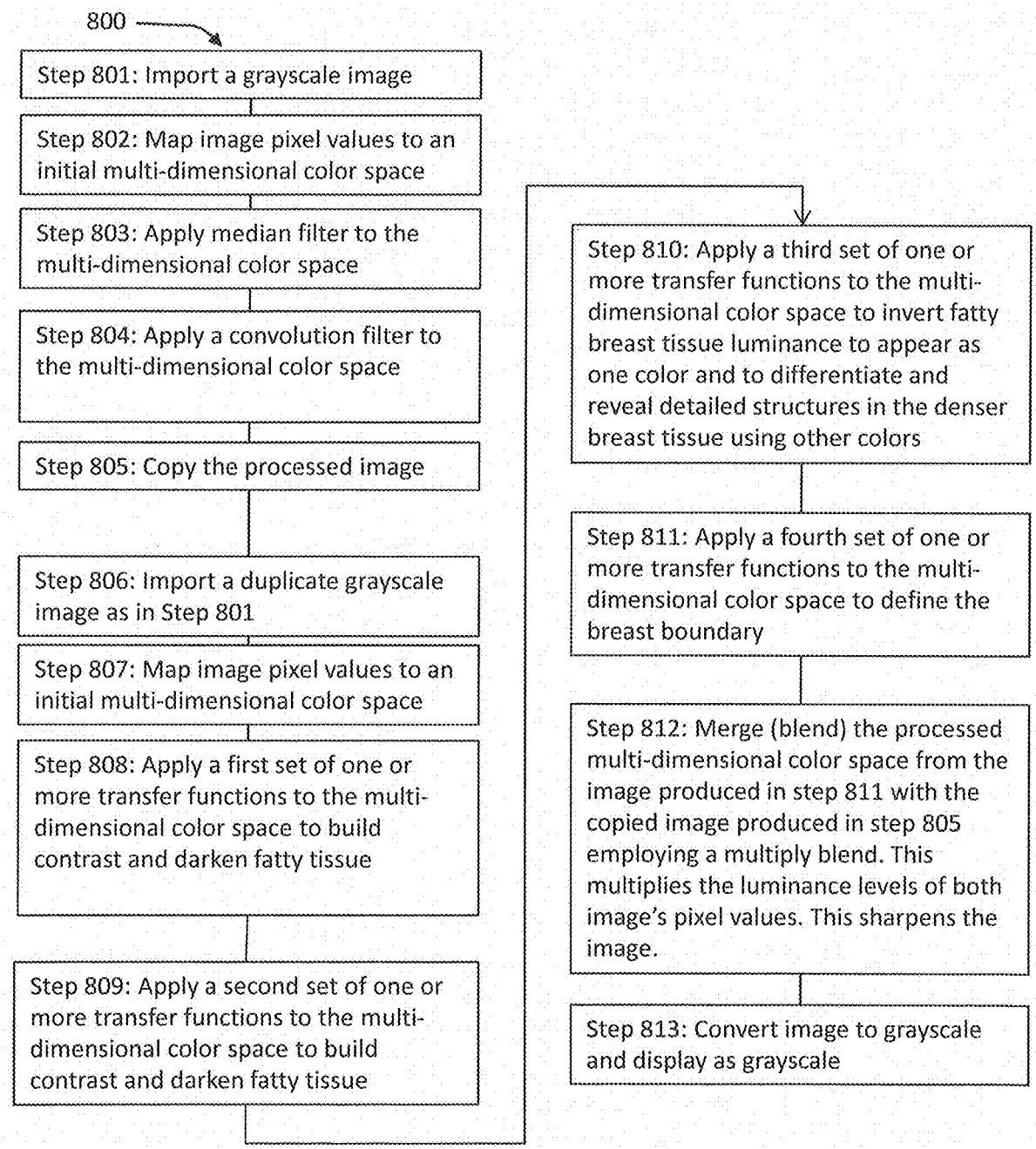

FIG. 8u is a flow chart illustrating a method 800 for creating a RF visualization from a grayscale image, according to at least one embodiment of the invention.

FIGS. 8b to 8c to 8l to 8m to 8s illustrate the results obtained by applying multiple local micro-contrast convergence transformations iteratively beginning with an original mammogram at FIG. 8a. FIGS. 8e to 8f to 8n to 8o and 8t illustrate the results of the same RF transformational sequence steps as applied to an original gradient grayscale image at 8d.

FIGS. 8g, 8h, 8p, and 8q show the color values of the RF PLUT (look-up tables) that have been optimized to reveal breast structures in mammographic images. FIGS. 8i, 8j, 8k and 8r show graphic representations in a coordinate system (e.g., that can be created from the PLUTs in FIGS. 8g, 8h, 8p, and 8q.

At step 801, processor 252 imports a grayscale image. FIG. 8a shows an exemplary grayscale image of a mammogram, according to at least one embodiment of the invention.

At step 802, processor 252 maps the original grayscale image to a multi-dimensional color space.

At step 803, processor 252 applies a median filter of radius 1 to the multi-dimensional color space of the original grayscale image.

At step 804, processor 252 applies a convolution filter to the multi-dimensional color space of the original image. In some embodiments, convolution filtering can be used to modify the spatial frequency characteristics of an image.

In operation, the convolution filter 804 is applied to each pixel in the multi-dimensional color space by replacing each pixel value with a weighted average of the pixel value and its neighboring pixel values. The pattern of neighboring pixel values is called the "window", which is applied, pixel by pixel, over the entire image. In some embodiments, the convolution filter is a 3×3 or radius=1 convolution filter. In other embodiments, matrix combinations such as 5×5, 8×8 can be used.

In one embodiment, the values of the 3×3 convolution filter matrix are shown in Table 1 as follows:

TABLE 1

| -4 | -1 | 0 |
|---|---|---|
| 0 | 1 | -1 |
| 6 | 0 | 1 |

At step 805, processor 252 copies the multi-dimensional color space of the processed image after step 804.

At step 806, processor 252, imports a duplicate of the same grayscale original image as utilized at step 801.

At step 807, processor 252 maps the duplicate image to a multi-dimensional color space.

At step 808, processor 252 applies a first set of one or more transfer functions (e.g., local micro-contrast convergence transfer function RF PLUT 1) to the multi-dimensional color space of the duplicate image. In these embodiments, a first transfer function (e.g., of local micro-contrast convergence function RF PLUT 1) is applied to the luminance color space 814 to elevate darker values of the image and attenuate mid tones.

In these embodiments, a second transfer function (e.g., of local micro-contrast convergence function RF PLUT 2 is applied to the luminance color space 815 to further attenuate mid tones. In these embodiments, mid tones are attenuated to a minimum at a luminance value of 1 in an image of 8-bit grayscale luminance range (0-255). In some embodiments, fatty tissue is elevated slightly at a maximum peak level 47 and transformed to 71. As a result, fatty tissue 816 is separated from the dense areas of the breast 817.

FIGS. 8i, 8j, 8k and 8r show Cartesian plots illustrating a representation of an exemplary PLUT transfer function (e.g., and generated from PLUTs applied by the processor 252) according to at least one embodiment of the invention. In these Cartesian plots, the color spaces, coordinates, and values have been previously described and illustrated in FIG. 2a.

FIG. 8b shows an exemplary image of a mammogram based on the multi-dimensional color space after applying the first set of one or more transfer functions to elevate darker values of the image and attenuate mid tones, according to at least one embodiment of the invention.

FIG. 8c shows an exemplary image of a mammogram based on the multi-dimensional color space after applying a second set one or more transfer functions to further attenuate mid tones, according to at least one embodiment of the invention.

In FIG. 8l, at step 810, processor 252 applies a third set of one or more transfer functions (e.g., local micro-contrast convergence function RF PLUT 3) to the multi-dimensional color space of the image in FIG. 8c to result in image shown in FIG. 8l. In these embodiments, the third transfer function is applied to the luminance color space 818 create a discontinuous invert in the luminance values.

In these embodiments, other "color" functions 819 of the third set of transfer functions can be applied to the color space layers to add subtle color hues.

At step 811, processor 252 applies a fourth set of one or more transfer functions (e.g., local micro-contrast convergence function RF PLUT 4) to the multi-dimensional color space of the image in FIG. 8l to result in image shown in FIG. 8m. In some embodiments, the RF PLUT 4, also shown graphically in FIG. 8q, is applied to the luminance channel 820 to create an increase in the luminance values of the lower densities of the image and to expand the tonal values associated with cancer and further define the breast boundary.

At step 812, processor 252 merges the processed multi-dimensional color space from the image in step 811 (e.g., FIG. 8m) with the copied image from step 805 (e.g., FIG. 8a) by employing a multiply blend. In some embodiments, the two images are blended with an opacity of 100%. As a result, the merged image has an emphasis on high frequency structures and attenuation of low frequency information with the highest densities remaining in color.

In these embodiments, and other embodiments employing a merging function, the merging function can be utilized to allow mathematical functions to be applied to one or more resultant images that utilize optimal qualities from each of the combining images for a specific purpose. For example, an image expressing the boundaries of cancer tissue in an image may be combined with an image expressing high frequency information. Such a combination can simultaneously show the extent of a cancer as it relates to possible high-frequency structures such as spiculations and calcifications within the tumor.

FIG. 8t shows an exemplary image of a mammogram after, at step 812, merging of the color spaces of the two images from 805 and 811, applying a merging function of 50%, and converting to grayscale at step 813 according to at least one embodiment of the invention.

In some embodiments, an image can be superimposed with additional matrices (layers) that contain either additional images or processing functions such as convert to black and white or incorporate layers generated from previous processing such as from high-pass filtering. Features include, but are not limited to, create new, paste, flatten, duplicate, make adjustment layer, and merge functions.

GI Algorithm

Embodiments of the invention regarding the GI algorithm provide visualizations that are designed to isolate, visualize, and characterize high-density structures and details in an image (e.g., original mammogram), and display them in a grayscale resultant image. Variations within the dense breast tissue are reflected in the darker areas of the image. Structures such as cancerous and benign lesions are clearly defined as are structures within high density areas. In some embodiments, the GI visualization is designed to improve visibility of abnormalities by a user (e.g., radiologist).

Figure 9Q:
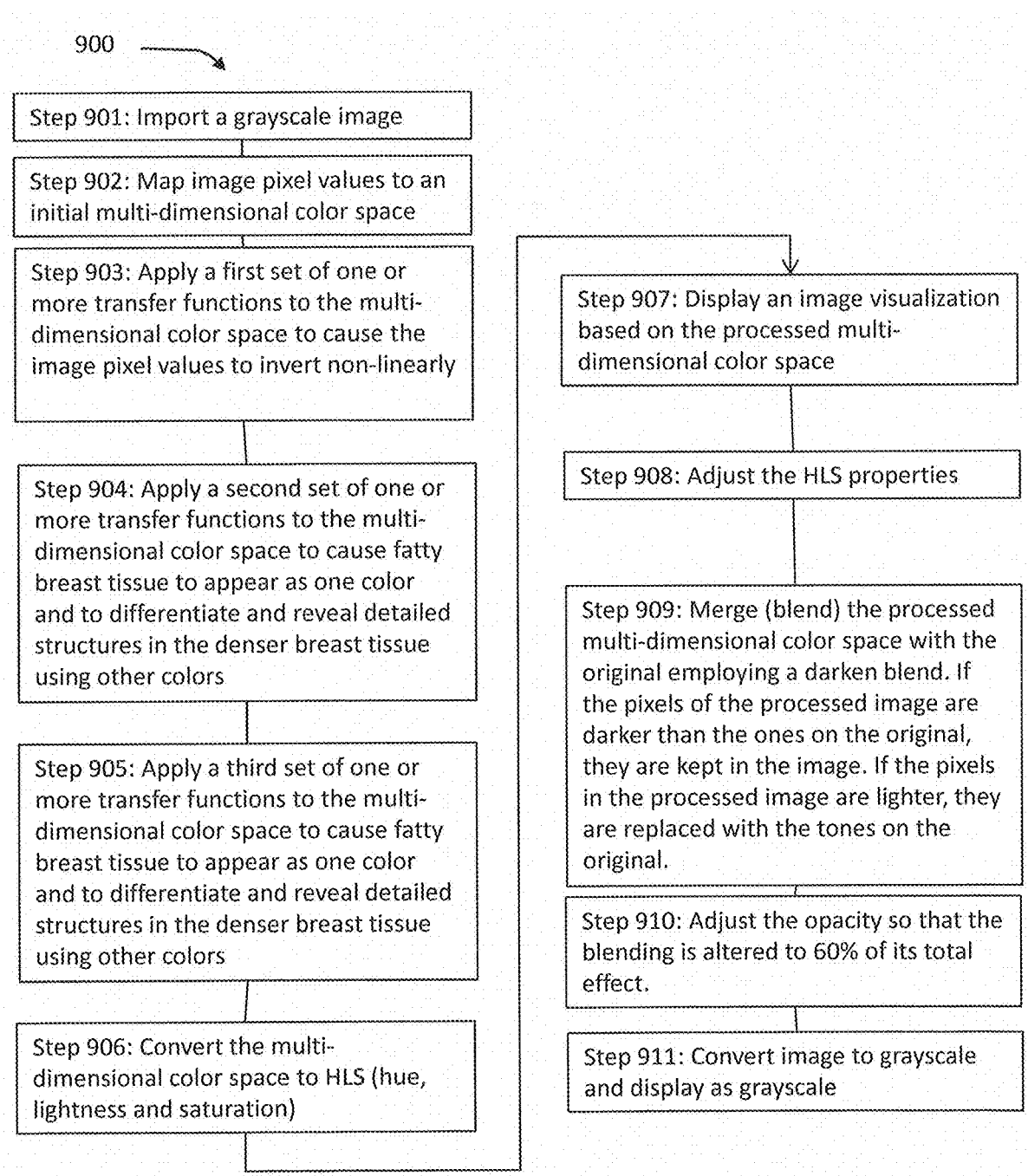

FIG. 9q is a flow chart illustrating a method 900 for creating a GI visualization from a grayscale image, according to at least one embodiment of the invention.

FIGS. 9b to 9c to 9m to 9n illustrate the results obtained by applying multiple local micro-contrast convergence transformations iteratively beginning with an original mammogram at FIG. 9a. FIGS. 9e to 9f to 9o to 9p illustrate the results of the same RF transformational sequence steps as applied to an original gradient grayscale image at 9d.

FIGS. 9g to 9h to 9k show the color values of the RF PLUT (look-up tables) that have been optimized to reveal breast structures in mammographic images. FIGS. 9i, 9j, and 9l show graphic representations in a coordinate system (e.g., that is created from the PLUTs in FIGS. 9g, 9h, and 9k respectively).

Referring now to FIG. 9q, at step 901, processor 252 imports a grayscale image. FIG. 9a shows an exemplary grayscale image of a mammogram, according to at least one embodiment of the invention.

At step 902, processor 252 maps the original grayscale image to a multi-dimensional color space.

At step 903, processor 252 applies a first set of one or more transfer functions (e.g., local micro-contrast convergence transfer function GI PLUT 1) to the multi-dimensional color space of the image. In these embodiments, one or more transfer functions are applied to the luminance color space 912 to non-linearly invert the luminance values of the image (e.g., as can be seen in FIG. 9g GI PLUT 1 lookup table and graphic representation of the PLUT in FIG. 9i).

At step 904, processor 252 applies a second set of one or more transfer functions (e.g., local micro-contrast convergence function FIG. 9h GI PLUT 2) to process the multi-dimensional color space image illustrated in FIG. 9b.

FIG. 9c shows an exemplary image of a mammogram based on the multi-dimensional color space after performing step 904 to further isolate high-density areas of the mammogram, according to at least one embodiment of the invention.

The process performed at step 904 discontinuously alters the luminance channel 913 while adding color to the image with a discontinuous mapping of the red channel 914, and a low value non-linear set of values in the green channel 915. In these embodiments, the resultant image in FIG. 9c shows that the low-density tones are colored orange. In some embodiments, the red values of the low densities have values between 174 to 175 depending on the distribution in the original image. High density areas are bright, and boundaries of high density areas become dark.

At step 905, processor 252 applies a third set of one or more transfer functions (e.g., local micro-contrast convergence function GI PLUT 3) to the multi-dimensional color space of the image in FIG. 9c to result in image shown in FIG. 9m. In these embodiments, the third transfer function is applied to the luminance channel 916 to amplify the low, mid, and high values with attenuated values between the amplified values as seen in FIGS. 9k and 9l. This greatly separates tonal values in the resultant image and separates the breast from the background, emphasizes possible cancerous areas of the breast, and further defines the core of possible lesions in blue 918. The values in some lesions have a value of blue=200+/−5.

The red channel 917 of the third set of transfer functions are applied to the color space layers to add distinctive color hues to the breast 919.

The color image shown in FIG. 9m is now converted to an HSL color space in step 904 with RGB values being converted to luminance, hue, and saturation values. The image can be displayed first in RGB color or after conversion in HSL color space in step 906.

The resultant image (e.g., FIG. 9n) can be displayed in step 907 based on the processed multi-dimensional color space.

The image in FIG. 9m is altered in step 908 by setting the saturation for all hues in the HSL color space to −100% saturation. As a result, hue is no longer a factor in the expression of the image.

In step 909, the desaturated HSL color image in FIG. 9m is merged (blended) with the original image in FIG. 9a employing a darken blend. If the pixels of the processed image are darker than the ones on the original image, they are kept in the image. If the pixels in the processed image are lighter, they are replaced with the tones on the original.

In step 910, processor 252 adjusts the opacity so that the blending is altered to 60% of its total effect.

The blended and then merged image is then converted to a single luminance channel to form a grayscale image as shown in FIG. 9n. Details in the final image reveal a large cancerous tumor in the upper part of the breast. The GI local micro-contrast convergence algorithmic process has revealed the extent of the lesion 920, defined its boundaries, and revealed details within the core of the lesion. Use of other local micro-contrast convergence algorithmic sequences embodied in this document, can then be correlated to the identified area for further analysis and to discriminate between normal high-density tissues, benign, and cancerous lesions.

The image can be converted to a single channel image containing luminance only in step 911 using a weighted conversion of R, G, and B values to achieve a luminance value according to the following formula: 0.30*R+0.59*G+0.11*B=luminance value.

RB Algorithm

Embodiments of the invention regarding the RB algorithm provide visualizations that are designed to isolate and clearly defined boundary and internal structures within high density areas of the breast including those of cancer while the rest of the breast is revealed as a dark gray.

Figures 10Q, 10R, 10S, 10T, 10V:
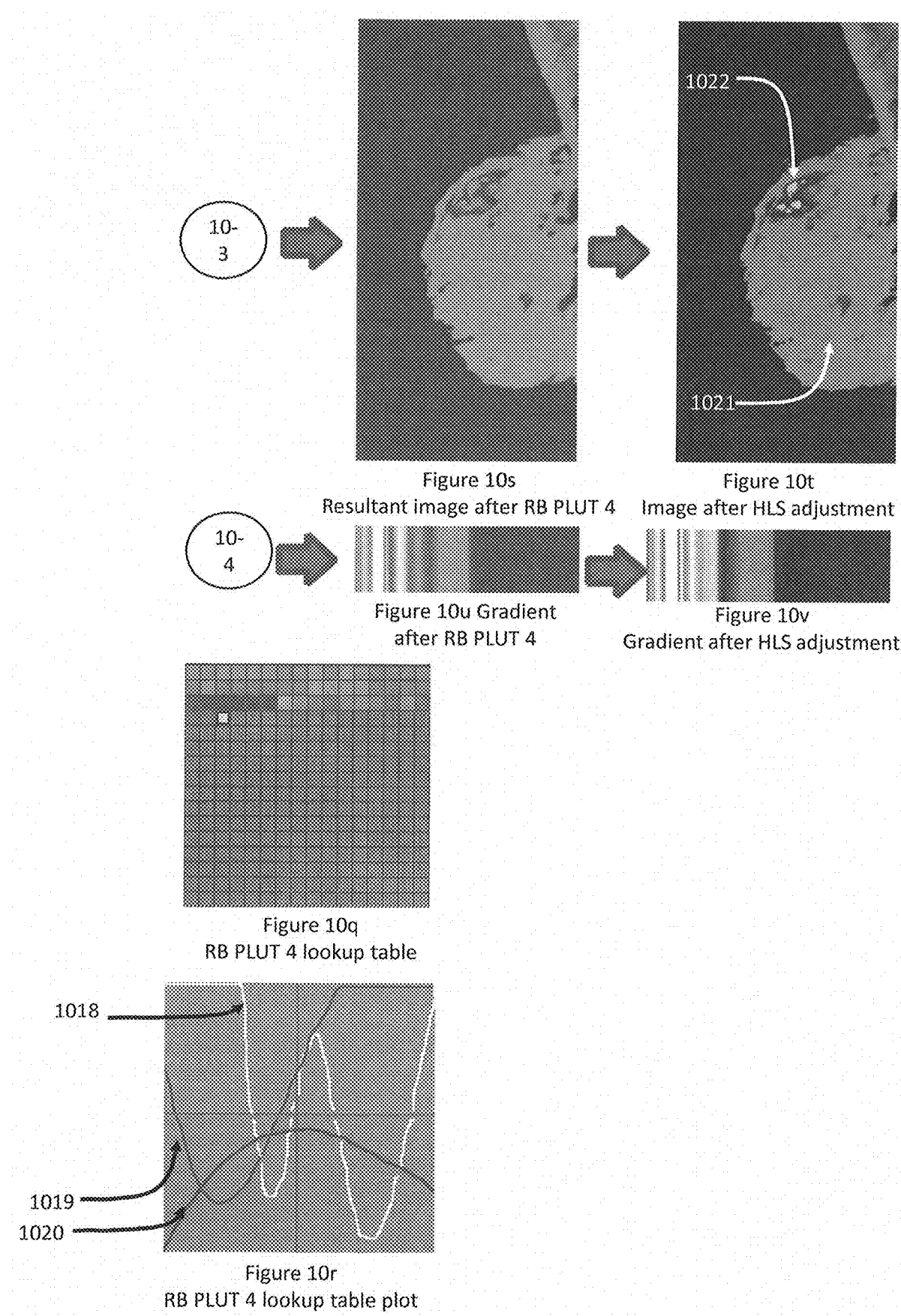
FIGS. 10a to 10w show an exemplary local micro-contrast convergence algorithmic sequence to process mammographic images to isolate breast abnormalities in resultant grayscale images according to at least some embodiments of the invention.
Figure 10W:
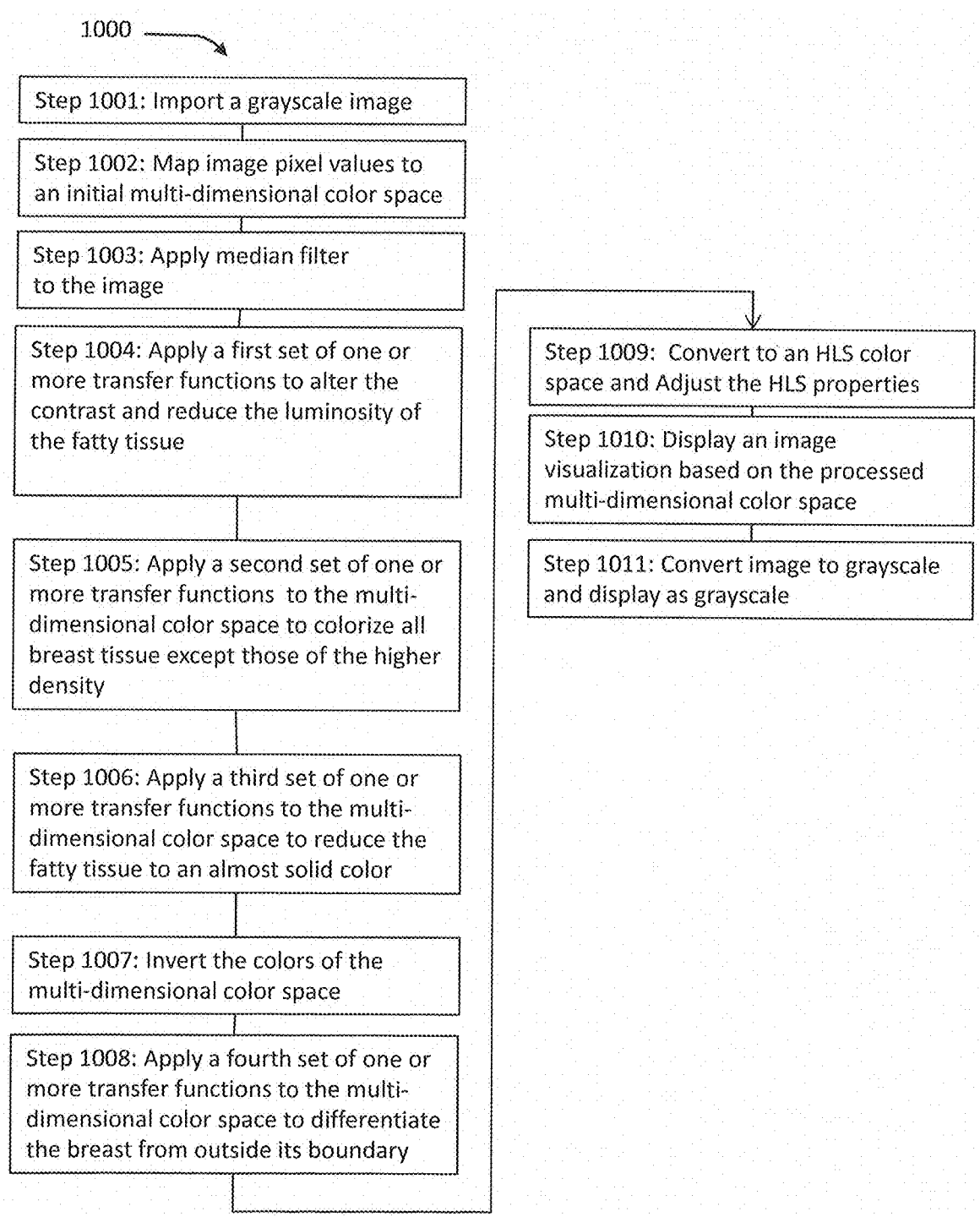

FIG. 10w is a flow chart illustrating a method 1000 for creating a RB visualization from a grayscale image, according to at least one embodiment of the invention.

FIGS. 10b to 10c to 10m to 10n to 10s to 10t illustrate the results obtained by applying multiple local micro-contrast convergence transformations iteratively beginning with an original mammogram at FIG. 10a. FIGS. 10e to 10f to 10o to 10p, to 10u to 10v illustrate the results of the same RB transformational sequence steps as applied to an original gradient grayscale image as shown in FIG. 10d.

FIGS. 10g, 10h, 10k, and 10q show the color values of the RB PLUT (look-up tables) that have been optimized to reveal breast structures in mammographic images. FIGS. 10i, 10j, 10l, and 10r show graphic representations in a coordinate system (e.g., that is created from the RB PLUTs in FIGS. 10g to 10h, 10k, and 10q respectively).

At step 1001, processor 252 imports a grayscale image. FIG. 10a shows an exemplary grayscale image of a mammogram, according to at least one embodiment of the invention.

At step 1002, processor 252 maps the original grayscale image to a multi-dimensional color space.

At step 1003, processor 252 applies a median filter of radius 3 to the multi-dimensional color space of the original grayscale image.

At step 1004, processor 252 applies a first set of one or more transfer functions (e.g., a local micro-contrast convergence transfer function RB PLUT 1) to the multi-dimensional color space of the duplicate image. In these embodiments, first set of one or more transfer functions (as shown in FIG. 10g and luminance transfer function 1012 of FIG. 10i) is designed to the discontinuously darken the luminance channel 1012 to darken the low- and mid-density areas values of the image as shown in FIGS. 10b and 10e.

In these embodiments, at step 1005, processor 252 applies a second set of one or more transfer functions (e.g., local micro-contrast convergence function RB PLUT 2) 10h to the multi-dimensional color space. For example, in FIG. 10j, transfer functions are applied to the luminance 1013, red 1014, and blue 1015 color space layers. FIG. 10c shows an exemplary image of a mammogram based on the multi-dimensional color space after applying a second set of one or more transfer functions, according to at least one embodiment of the invention.

The luminance channel is altered to increase the contrast of the image. The red channel discontinuously elevates the dark areas of the image, reduces the highlights, and "flat-lines" the mid tones. The blue channel is reduced in value to control tonal values in the color image.

At step 1006, processor 252 applies a third set of one or more transfer functions (e.g., third local micro-contrast convergence function RB PLUT 3 FIG. 10k and plot 101) to the multi-dimensional color space of the image in FIG. 10c to produce the image shown in FIG. 10m. In some embodiments, a transfer function is applied to the luminance channel 1016 to create a discontinuous "flat line" in the low-density areas of the image, attenuates the mid-tones, and slightly reduces the high-density luminance values. The red, green, and blue channels 1017 have transfer functions applied that colorize the low-density areas of the breast area. In these embodiments, other "color" functions of the third set of transfer functions are applied to the color space layers to add uniform color hues to the breast image.

At step 1007, the colors of the image shown in FIG. 10m are inverted to create resultant image in FIG. 10n in the mammogram and 10p in the gradient.

At step 1008, processor 252 applies a fourth set of one or more transfer functions (e.g., fourth local micro-contrast convergence function RB PLUT 4) 10q to the multi-dimensional color space image in FIG. 10n to result in the image shown in FIG. 10s. FIG. 10r shows that the luminance values 1018 of the low densities are brought to a maximum 255 level for all luminance values <74, another peak for mid-tones and for the brightest areas of the image. The red channel 1019 attenuates the low densities while maximizing the high densities with values set at 255 for all luminance values >160. The green channel 1020 contributes to the color hues of background and breast tissues. In these embodiments, the RB PLUT 4 FIG. 10q, also shown graphically in FIG. 10r, is applied to the luminance color space to differentiate the breast from the outside of its boundary.

At step 1009, the color image shown in FIG. 10s is converted to an HSL color space with RGB values being converted to luminance, hue, and saturation values. The image can be displayed first in RGB color or after conversion in HSL color space at step 1010. An exemplary HSL color space conversion is as follows:

(Hue, Saturation, Lightness, Zone)
(0.0, −1.0, −0.3, Magenta)
(0.0, −1.0, 0.3, Red)
(0.0, −1.0, −0.4, Yellow)
(0.0, −1.0, −0.4, Cyan)
(0.0, −1.0, 0.2, Blue)
(0.0, −1.0, −0.1, Green)

The final image in FIG. 10t is created from the image in FIG. 10s by setting the master saturation for all hues in the HSL color space to −100% saturation. As a result, hue is no longer a factor in the expression of the image. Luminance values however, are still adjustable and changing the luminance values of various hues in the color space can alter the grayscale representation of those values.

In step 1011, the image is converted to a single channel image containing luminance only. In this embodiment, all areas of non-pathology are revealed in the uniform gray 1021 of the breast image area where the average luminance value may be 130. This separation of possible areas of abnormalities 1022 reduces the "dwell time" for a radiologist, that is, the time they must spend investigating all areas of an image to locate the highest probability areas where cancer could occur.

Consistency of Local Micro-Contrast Convergence Algorithm

FIGS. 11a through 11d illustrate the consistency with which one embodiment of this application performs across different imaging modalities. The pattern responses for breast images reveal consistent colors and tissue characterizations for modalities 3D Tomosynthesis in FIG. 11a, synthetic 2D from 3D in FIG. 11b, Full Field Digital Mammography (FFDM) in FIG. 11c, and digitized film in FIG. 11d. This provides a radiologist and their patients the ability to compare changes over time using only one set of algorithms, even when a patient's images were generated historically using different imaging modalities. These results verify one of the capabilities inherent in the local micro-contrast convergence approach as indicated in the local micro-contrast convergence hierarch of features identified as Modality Fusion in FIG. 1d.

Figure 11A:
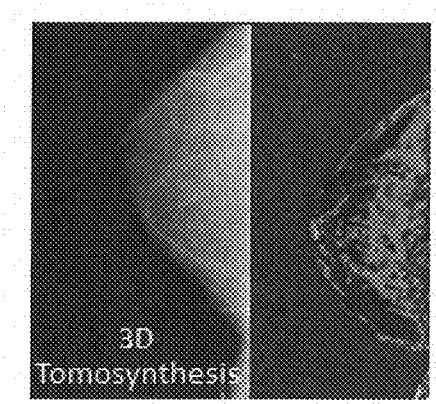
FIGS. 11a to 11d shows an exemplary local micro-contrast convergence algorithmic sequence applied to four different mammograms generated from four different image acquisition modalities showing the same patterns from one local micro-contrast convergence algorithm according to at least some embodiments of the invention.
Figure 11C:
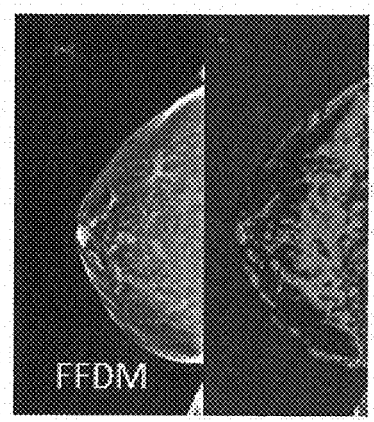
Figure 11B:
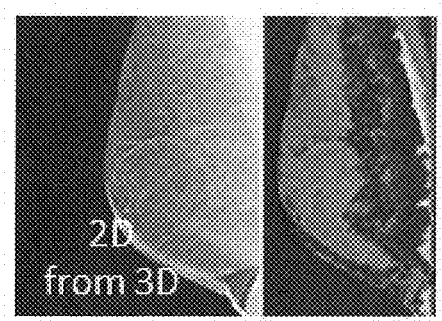
Figure 11D:
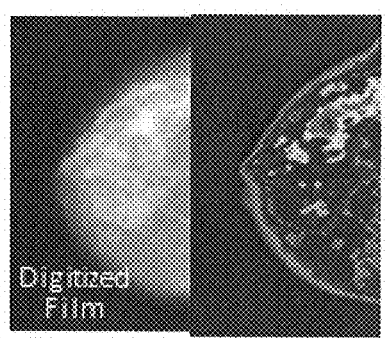
Figure 11E:
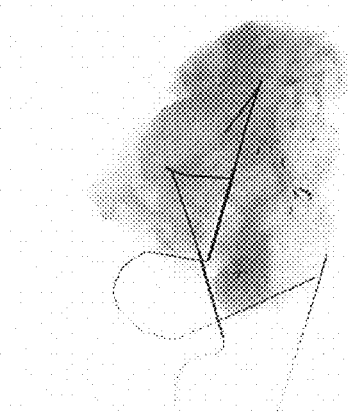
FIG. 11e shows an X-ray image of surgically excised breast cancer tissue.
Figure 11F:
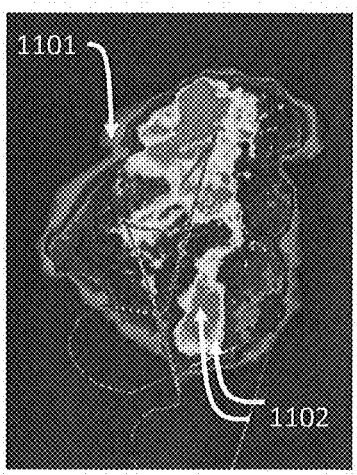
FIG. 11f shows the results after applying an exemplary local micro-contrast convergence algorithmic sequence to the X-ray in FIG. 11e according to at least some embodiments of the invention.

FIG. 11e shows an X-ray view of cancer in an exemplary mammogram image generated from excised breast tissue removed in surgery. FIG. 11f shows an exemplary mammogram image after processing the image using one or more methods described herein. The original image was processed using the CI Algorithm described earlier in this document. The black and magenta boundaries of the cancer 1101 are clearly defined, as are the changes in color inside of the boundaries 1102 indicating the extent of cancer development.

Embodiments of the invention, described herein, include methods that utilize a multi-algorithmic, multi-dimensional, computer-based process for the visualization and characterization of features, in context, in images. These local micro-contrast convergence methods are applicable in applications where the features are less than 1 mm in size, less than 900 microns in size, less than 850 microns in size, less than 800 microns in size, or less than 750 microns in size.

Figure 11G:
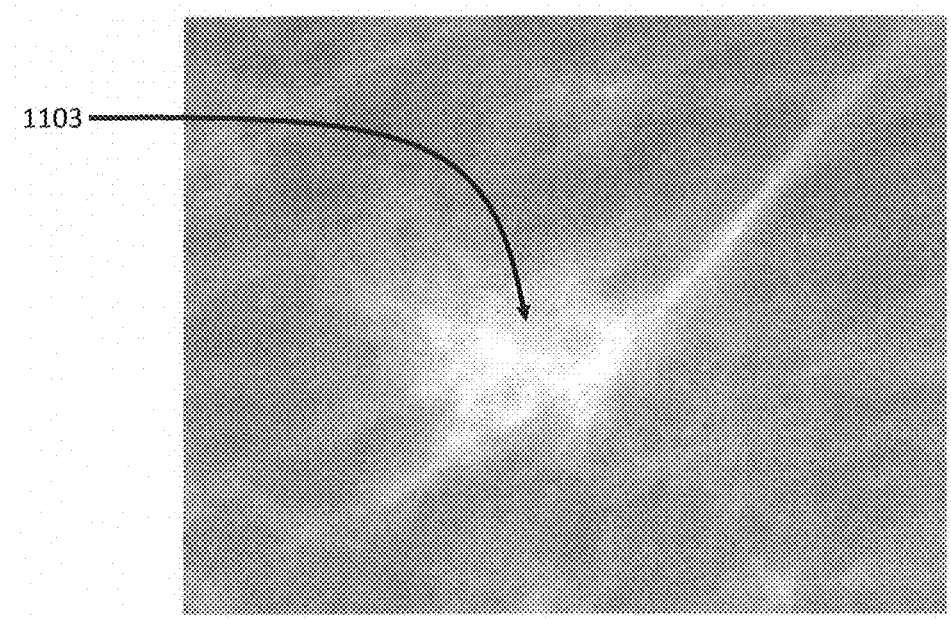
FIG. 11g shows a close-up of a mammographic X-ray image revealing the presence of cancer.
Figure 11H:
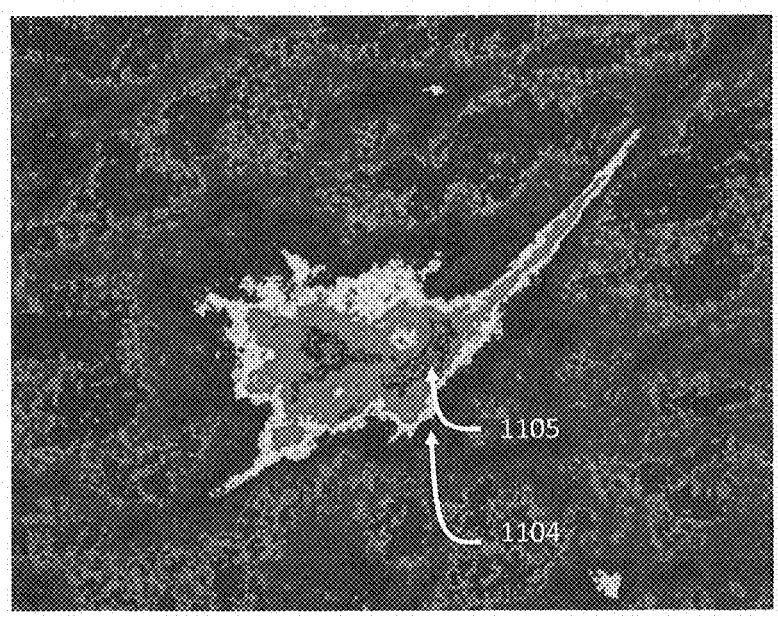
FIG. 11h shows the results after applying an exemplary local micro-contrast convergence algorithmic sequence to the X-ray in FIG. 11g.
Figure 12:
FIG. 12 shows an exemplary image of a non-human animal after application of at least one embodiment of the invention.

FIG. 11g shows an enlarged view of a mammographic X-ray known to contain cancer 1103. FIG. 11h shows an exemplary mammogram image after processing the image using one or more of the methods described herein. In FIG. 11h, the black boundary of the cancer 1104 using the CI Algorithmic process described earlier in FIGS. 4a-4k is clearly defined as are details inside of the core of the cancer. The progression from yellow, to red to blue within the cancer show a progression cancer development to as small a size in the blue core 1105 being a size of only 980 microns. Multiple algorithmic expressions that are embodiments of the invention provide different characterizations and visualizations of the same tissue.

These methods are even applicable in applications where a feature of interest is located within another feature, where the feature of interest is less than 900 microns in size, less than 850 microns in size, less than 800 microns in size, or less than 750 microns in size and where the first feature is 1 mm in size or larger. In some embodiments, the feature of interest is between 700 and 900 microns in size.

In some embodiments, structures as small as 750 II. (microns) are identified using the above methods. Based on X-ray images where a pixel represents a dimension of breast tissue that is 75 II. in size, cancer cores can be expressed and characterized in sizes from 750 II. to 1 mm. It has been determined, through clinical testing, that structures as small as 500 II. (microns) can be revealed and differentiated in images whose pixel dimensions are 50 II. or smaller. Consequently, cancer of various forms as well as Ductal Carcinoma in Situ and precancerous Atypical Hyperplasia have been revealed using these methods.

Alternative Embodiments—Different Processing Combinations

While the preceding paragraphs describe different embodiments for image visualization of local micro-contrast convergence, one of ordinary skill in the art will appreciate that one or more of the processing steps performed in one embodiment may be applied in any order and/or to other embodiments, including, but not limited to: gamma level adjustment or leveling, convolution filtering, sharpening filters, smoothing filters, median filters, high-pass filters, low-pass filters, merging functions, image multiplication functions, image subtraction functions, image addition functions, image blending functions, wavelet functions, and image layering functions, among others described herein.

Alternative Embodiments—Different Modalities

Embodiments of the invention have applicability to a number of different fields, including, but not limited to: medical imaging (e.g., mammography, MRI, PET or CAT scans, ultrasound, 3-D Tomosynthesis), bomb detection, liquid explosive detection, satellite imaging, structural analysis, industrial, stress, quality control, weld and material analysis (e.g., checking for cracks or breaks in high-tension wires, airplane wings, pipes in nuclear power plants), printing standards analysis (e.g., money stamps), and forensics, among others. Thus, different imaging modalities (e.g., mammogram, x-ray, ultrasound, infra-red, ultra-violet, Mill, CT scans, PET scans, grayscale, color, visible light (e.g., photo microscopy), laser scans) may be processed using different visualization methodologies described herein. One of ordinary skill in the art would also appreciate that embodiments of the invention are not limited to the fields described herein, but instead are applicable to any field requiring pixel data analysis in an image, regardless of the imaging modality or energy source generating the images.

Alternative Embodiments—Cancer/Diseases

Embodiments of the invention have applicability to visualizing, characterizing, and detecting several different cancers including, but not limited to: prostate, kidney, liver, bone, lung, brain, and skin of both humans and animals. One of ordinary skill in the art would also appreciate that embodiments of the invention are not limited to the cancers described herein, but instead are applicable to other similar cancers.

Embodiments of the invention have applicability to detecting several different diseases including, but not limited to: cardiovascular diseases, detection of Alzheimer's disease in retinal scans, diseases of the eye, multiple sclerosis lesion mapping, photo microscopy. One of ordinary skill in the art would also appreciate that embodiments of the invention are not limited to the diseases described herein, but instead are applicable to other similar diseases.

Embodiments for Improving False Positive/False Negative Rates

Applying one or more of the micro-contrast convergence algorithms, described herein in medical applications for example, produce an image visualization that facilitates users (e.g., radiologists) with detecting structures of interest (e.g., cancer). As a result, the false positive rates and false negative rates are considerably reduced.

In some embodiments, the false positive rate for breast cancer detection in a mammogram image, where the breast includes at least a portion of dense breast tissue, over a series of 100 trials, is less than 10% as determined by a physician. In some embodiments, the false positive rate for breast cancer detection in a mammogram image, where the breast includes at least a portion of dense breast tissue, over a series of 100 trials, is less than 5% as determined by a physician. In some embodiments, the false positive rate for breast cancer detection in a mammogram image, where the breast includes at least a portion of dense breast tissue, over a series of 100 trials, is less than 1% as determined by a physician.

In some embodiments, the false negative rate for breast cancer detection in a mammogram image, where the breast includes at least a portion of dense breast tissue, over a series of 100 trials, is less than 60% as determined by a physician. In some embodiments, the false negative rate for breast cancer detection in a mammogram image, where the breast includes at least a portion of dense breast tissue, over a series of 100 trials, is less than 50% as determined by a physician. In some embodiments, the false negative rate for breast cancer detection in a mammogram image, where the breast includes at least a portion of dense breast tissue, over a series of 100 trials, is less than 45% as determined by a physician. In some embodiments, the false negative rate for breast cancer detection in a mammogram image, where the breast includes at least a portion of dense breast tissue, over a series of 100 trials, is less than 40% as determined by a physician. In some embodiments, the false negative rate for breast cancer detection in a mammogram image, where the breast includes at least a portion of dense breast tissue, over a series of 100 trials, is less than 35% as determined by a physician. In some embodiments, the false negative rate for breast cancer detection in a mammogram image, where the breast includes at least a portion of dense breast tissue, over a series of 100 trials, is less than 30% as determined by a physician. In some embodiments, the false negative rate for breast cancer detection in a mammogram image, where the breast includes at least a portion of dense breast tissue, over a series of 100 trials, is less than 25% as determined by a physician. In some embodiments, the false negative rate for breast cancer detection in a mammogram image, where the breast includes at least a portion of dense breast tissue, over a series of 100 trials, is less than 20% as determined by a physician. In some embodiments, the false negative rate for breast cancer detection in a mammogram image, where the breast includes at least a portion of dense breast tissue, over a series of 100 trials, is less than 15% as determined by a physician. In some embodiments, the false negative rate for breast cancer detection in a mammogram image, where the breast includes at least a portion of dense breast tissue, over a series of 100 trials, is less than 10% as determined by a physician. In some embodiments, the false negative rate for breast cancer detection in a mammogram image, where the breast includes at least a portion of dense breast tissue, over a series of 100 trials, is less than 5% as determined by a physician. In some embodiments, the false negative rate for breast cancer detection in a mammogram image, where the breast includes at least a portion of dense breast tissue, over a series of 100 trials, is less than 4% as determined by a physician. In some embodiments, the false negative rate for breast cancer detection in a mammogram image, where the breast includes at least a portion of dense breast tissue, over a series of 100 trials, is less than 3% as determined by a physician. In some embodiments, the false negative rate for breast cancer detection in a mammogram image, where the breast includes at least a portion of dense breast tissue, over a series of 100 trials, is less than 2% as determined by a physician. In some embodiments, the false negative rate for breast cancer detection in a mammogram image, where the breast includes at least a portion of dense breast tissue, over a series of 100 trials, is less than 1% as determined by a physician.

In some embodiments, the false negative rate for breast cancer detection in a mammogram image, where the breast includes normal breast tissue, over a series of 100 trials, is less than 16% as determined by a physician. In some embodiments, the false negative rate for breast cancer detection in a mammogram image, where the breast is normal breast tissue, over a series of 100 trials, is less than 15% as determined by a physician. In some embodiments, the false negative rate for breast cancer detection in a mammogram image, where the breast includes normal breast tissue, over a series of 100 trials, is less than 10% as determined by a physician. In some embodiments, the false negative rate for breast cancer detection in a mammogram image, where the breast includes normal breast tissue, over a series of 100 trials, is less than 5% as determined by a physician. In some embodiments, the false negative rate for breast cancer detection in a mammogram image, where the breast includes normal breast tissue, over a series of 100 trials, is less than 1% as determined by a physician.

Feature Extraction

By implementing embodiments of the invention, images are generated that visualize and characterize tissue structures in an enhanced manner that improves feature identification (e.g., by radiologists).

In some embodiments, processor 252 may implement one or more computer aided detection (CAD) techniques on one or more generated image visualizations to identify cancerous structures. Large-scale pattern recognition systems applicable to millions of informational features may include such features first, second, and third order image analysis any may employ image comparisons (e.g., between a known cancerous structure and portions of the image visualizations).

The process employed in this application using local micro-contrast convergence algorithmic approaches causes such tissue type in an image, such as a mammogram, to assume characteristics color and grayscale properties that uniquely characterize the tissues and their boundaries, making feature identification and extraction highly effective for accurate identification. These properties include, but are not limited to: morphology, geometry, color, texture, relationships among different tissue structures (such as correlating the presence of lesions with microcalcifications in breast tissue), shapes of lesion boundaries, presence of spiculations, edge-gradients, cumulative edge-gradient distributions, architectural distortions, distribution of colors within lesions, contrast, temporal stability (changes between mammographic exams), and correlation of features between different views (multiple view correlation between CC and MLO mammographic image views).

The Machine Learning process in the breast cancer detection domain begins by extracting features correlated with disease such as benign cysts, fibroadenomas, carcinomas, and invasive cancers. A training set of images is used to develop criteria for comparison between cancer and non-cancer areas of a mammogram.

Relevant features are extracted as clusters of pixel luminance and color values that have resulted in local micro-contrast convergence process tissue characterization patterns from a given coordinate area in each processed image. A multiplicity of local micro-contrast convergence processed images can be analyzed and features extracted from each of the separate images that have been created through one or more visualization algorithmic sequences, described herein. All processed images being examined may be superimposed so there is complete registration in areas of interest among the different processed images.

In some embodiments, processor 252 may generate one or more non-linear transfer functions to apply to an image to identify a feature of interest. In these embodiments, processor 252 may run different trials, with a different set of local micro-contrast convergence transfer functions used for each trial. In some embodiments, the local micro-contrast convergence transfer functions may be generated at random. In some embodiments, the local micro-contrast convergence transfer functions are generated based on default functions (e.g., trigonometric functions). Examples for generating local micro-contrast convergence transfer functions based on default functions are illustrated in FIG. 2a.

The range of luminance values available for mapping luminance values in this coordinate plot is unbounded. As a result of the trials, processor 252 may select a preferred set of non-linear transfer functions to apply to an image based on the lowest probability of a false positive and/or false negative.

Feature analysis may include high separability feature extraction (HSFE) from data, basing on both standard and advanced characteristics of images and time series, including: Co-Occurrences, Gabor, SIFT, LBP, Histograms of Oriented Gradients, Random Ferns and Hough Forests.

Machine learning, data mining, and statistical modeling techniques can be applied for real-time object recognition and localization in the processed images using such processes as Adaboost, genetic programming, support vector machines, neural networks, global optimization, and learning vector quantization.

There is no theoretical limit to the number of features that can be extracted or the number of correlations that can be created among them. Algorithmic development can be employed for Big Data applications using R, Pig, Storm, MySQL, MongoDB, and Hadoop.

In at least one embodiment, there is included one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

What is claimed is:

1. A method of visualizing and characterizing a feature in an image, comprising:
    applying a first local micro-contrast convergence algorithm to a first image to produce a second image that is separate and distinct from the first image, wherein the second image includes the feature,
    wherein applying the first local micro-contrast convergence algorithm includes iteratively and sequentially applying each of a plurality of non-linear discontinuous transfer functions to a corresponding image in a sequential set of images including the first image and one or more intermediate images, wherein each subsequent image in the sequential set of images is generated by applying one of the plurality of non-linear discontinuous transfer functions to a previous image in the sequential set of images thereby resulting in generation of the second image to reveal and characterize, in the second image, the feature including a physical or biological structural visualized and characterized pattern that was present but undifferentiated in the first image; and
    wherein local micro-contrast convergence represents a sequence of transfer functions including the two or more non-linear discontinuous transfer functions wherein at least one of the two or more non-linear discontinuous transfer functions includes at least one discontinuity to cause neighboring pixel groups representative of specific structures to converge to cause relationships among neighboring pixel groups to aggregate into particular color and luminosity patterns,
    wherein the two or more non-linear discontinuous transfer functions including the at least one discontinuity cause the physical or biological structural visualized and characterized pattern to include a tissue feature differentiation,
    wherein the two or more non-linear discontinuous transfer functions including the at least one discontinuity cause the physical or biological structural visualized and characterized pattern to include a boundary of cancerous and benign tissue structures in the second image, and
    wherein the two or more non-linear discontinuous transfer functions including the at least one discontinuity cause the physical or biological structural visualized and characterized pattern to define an internal geometry of cancerous and/or benign tissue structures in the second image.

2. The method of claim 1, wherein the second image includes a second feature, and wherein the second feature within the first feature is 700-1500 microns in size.

3. The method of claim 2, wherein applying a first local micro-contrast tissue convergence algorithm to a first image to produce a second image that is separate and distinct from the first image includes:
    receiving the first image;
    mapping pixel values of the first image to a first initial multi-dimensional color space;
    applying one or more non-linear transfer functions to the first initial multi-dimensional color space to cause local micro-contrast convergence and to create a first processed multi-dimensional color space; and
    displaying an image visualization of the second image based on the first processed multi-dimensional color space.

4. The method of claim 3, wherein the multi-dimensional color space is one of: an RGB, HSV, HLS, HSB, XYZ, CMYK, CIEXYZ or CIELAB color space.

5. The method of claim 3, further comprising:
    applying a median filter to the first initial multi-dimensional color space; and
    wherein applying the one or more non-linear transfer functions to the first initial multi-dimensional color space includes:
    applying a first set of non-linear transfer functions to attenuate a first dense breast tissue and a second dense breast tissue wherein the second fatty breast tissue is denser than the first fatty breast tissue;
    applying a second set of non-linear transfer functions to cause dense breast tissue to appear as a first color, margin of tissue, and pixel pattern, and to differentiate the second dense breast tissues margins and pixel patterns using other colors;
    applying a third set of non-linear transfer functions to amplify low pixel values and attenuate high pixel values in the color space layer associated with the first color; and
    applying a fourth set of non-linear transfer functions to change the background of the image, when displayed, to black.

6. The method of claim 3, further comprising:
    receiving a second image;
    mapping pixel values of the second image to a second initial multi-dimensional color space;

applying a median filter and a convolution filter to the initial multi-dimensional color space to create a second processed multi-dimensional color space; and displaying an image visualization based on the first processed multi-dimensional color space associated with the first image and the second processed multi-dimensional color space associated with the second image, and wherein the applying the one or more non-linear transfer functions to the first initial multi-dimensional color space associated with the first image includes:

applying a first set of non-linear transfer functions to first pixel values and second pixel values of the first image, each of the first pixel values and the second pixel values having low tones, mid tones and high tones, the second pixel values being darker than the first pixel values, wherein applying the first set of non-linear transfer functions is configured to elevate darker second pixel values of the first image and attenuate mid tones of the first pixel values and the second pixel values;

applying a second set of non-linear transfer functions to the multi-dimensional color space to add color hues; and applying a third set of non-linear transfer functions to expand tonal values representative of cancer.

7. The method of claim 3, further comprising:

adjusting gamma levels of the multi-dimensional color space to adjust the contrast of the first image and highlight structural details, and wherein the applying the non-linear transfer functions to the first initial multi-dimensional color space associated with the first image includes:

applying a first set of non-linear transfer functions to diminish luminance levels of the multi-dimensional color space; and applying a second set of non-linear transfer functions to invert values of the initial multi-dimensional color space associated with luminance.

* * * * *